(12) United States Patent
Gilbert et al.

(10) Patent No.: US 9,115,088 B2
(45) Date of Patent: Aug. 25, 2015

(54) ANTI-MALARIAL AGENTS

(71) Applicant: MERCK PATENT GMBH, Darmstadt (GB)

(72) Inventors: Ian Hugh Gilbert, Dundee (GB); Neil Norcross, Dundee (GB); Beatriz Baragana Ruibal, Dundee (GB); Achim Porzelle, High Peak (GB)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/391,394

(22) PCT Filed: Mar. 14, 2013

(86) PCT No.: PCT/GB2013/050633
§ 371 (c)(1),
(2) Date: Oct. 9, 2014

(87) PCT Pub. No.: WO2013/153357
PCT Pub. Date: Oct. 17, 2013

(65) Prior Publication Data
US 2015/0045354 A1    Feb. 12, 2015

(30) Foreign Application Priority Data

Apr. 10, 2012  (GB) .................................. 1206280.8

(51) Int. Cl.
*A61K 31/5377*    (2006.01)
*A61K 31/541*    (2006.01)
*C07D 215/52*    (2006.01)

(52) U.S. Cl.
CPC .......... *C07D 215/52* (2013.01); *A61K 31/5377* (2013.01); *A61K 31/541* (2013.01)

(58) Field of Classification Search
None
See application file for complete search history.

(56) References Cited

U.S. PATENT DOCUMENTS 2,502,264 A    3/1950  Lutz et al.

OTHER PUBLICATIONS

Boa, Andrew N. et al., "Synthesis of brequinar analogue inhibitors of malaria parasite dihydroorotate dehydrogenase", Bioorganic & Medicinal Chemistry, vol. 13, No. 6, 2005, pp. 1945-1967, XP002698185, compounds 17-23.
Kumar, Gyanendra et al., "Discovery of a Rhodanine Class of Compounds as Inhibitors of", Journal of Medicinal Chemistry, vol. 50, No. 11, 2007, pp. 2665-2675, XP002698186, table 4; compound 56.
Freitag, Marcus et al., "Synthesis and antiplasmodial activity of new N-[3-(4-{3-[(7-chloroquionlin-4-yl)amino]propyl} piperazin-1-yl)propyl]carboxamides", Biogranic & Medicinal Chemistry, vol. 15, No. 7, 2007, pp. 2782-2788, XP002698187, table 1; compounds 5a, 5b, 5r.
Gamo, Francisco-Javier et al., "Thousands of chemical starting points for antimalarial lead identification", Nature, vol. 465, 7296, pp. 305-310, XP002698188, the whole document.
Spinks, Daniel et al, "Investigation of Trypanothione Reductase as a Drug Target in *Trypanosoma brucei*", Chemmedchem, vol. 4, No. 12, 2009, pp. 2060-2069, XP002698189, abstract; table 2.
International Search Report, PCT/GB2013/050633, dated Jun. 4, 2013.

*Primary Examiner* — Alicia L Otton
(74) *Attorney, Agent, or Firm* — Ward and Smith, P.A.

(57) ABSTRACT

The present invention relates to a novel class of quinolone-4-carboxamide Pf3D7 inhibitors of general formula (I) (Formula (I)) wherein $R^1$, $R^2$, $R^3$, $R^4$, $R^5$, $R^6$, $R^7$, $R^8$ and X are as defined herein, to their use in medicine, and in the treatment of malaria in particular, to compositions containing them, to processes for their preparation and to intermediates used in such processes.

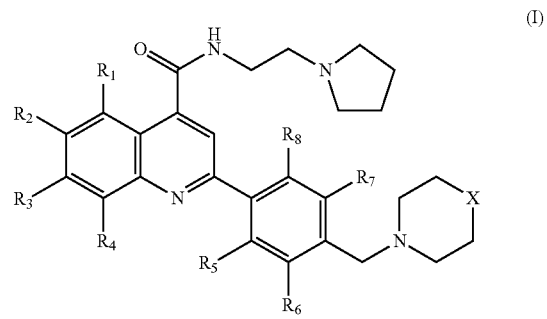

21 Claims, 4 Drawing Sheets

ANTI-MALARIAL AGENTS

CROSS REFERENCE TO RELATED APPLICATIONS

This application is a 35 U.S.C. §371 U.S. national phase entry of International Application No. PCT/GB2013/050633 having an international filing date of Mar. 14, 2013, which claims the benefit of Great Britain Application No. 1206280.8, filed Apr. 10, 2012, each of which is incorporated herein by reference in its entirety.

FIELD OF THE INVENTION

The present invention relates to a new class of quinoline-4-carboxamide compounds, to their use in medicine, to compositions containing them, to processes for their preparation and to intermediates used in such processes. In particular the present invention provides quinoline-4-carboxamide for use in the treatment of malaria.

BACKGROUND

In the undeveloped world, over 350 million people are at risk from neglected tropical diseases such as malaria, African sleeping sickness, Chagas disease and Leishmaniasis. Existing therapies to treat such neglected tropical diseases are increasingly ineffective due to the development of resistance by the parasites that underpin these conditions to drugs used both in disease prevention and treatment.

Worldwide, an estimated 200 to 300 million malarial infections occur each year. Approximately 1 million people die each year from malaria and the disease is one of the world's biggest killers. Malaria is caused by an infection of the red blood cells with a tiny organism or parasite called protozoa. Five species of the protozoa *Plasmodium* are known to cause infection in humans: *Plasmodium falciparum* (Pf); *Plasmodium vivax* (Pv); *Plasmodium ovale*; *Plasmodium malariae*; and *Plasmodium knowlesi*. The injection of protozoa of *Plasmodium falciparum, Plasmodium vivax, Plasmodium ovale*, or *Plasmodium malariae* into the blood stream, is effected by a single source, the bite of the female *Anopheles* mosquito. Thus there is a need for agents which are effective against *Plasmodium falciparum, Plasmodium vivax, Plasmodium ovale, Plasmodium malariae* and *Plasmodium knowlesi* infections.

The most life-threatening form of malaria is attributable to blood cells infected with the *Plasmodium falciparum* parasite, and can cause kidney or liver failure, coma and death. About 2% of people infected with *falciparum* malaria die and with an estimated one child dying every 45 seconds from *falciparum* malarial infections the need for an effective treatment could not be higher. Thus there is a need for agents which are: effective against *Plasmodium falciparum* infections; effective against *Plasmodium falciparum* and *Plasmodium vivax* infections; effective against *Plasmodium falciparum, Plasmodium vivax, Plasmodium malariae, Plasmodium ovale* and *Plasmodium knowlesi* infections.

*Plasmodium* species require two hosts, human and mosquito for completion of its life-cycle. In humans the infection is initiated by the inoculation of sporozoites in the saliva of an infected mosquito. Once inside the body the sporozoites migrate to the liver and there infect hepatocytes where they differentiate, into the exoerythrocytic intracellular stage, into the merozoite stage which infects red blood cells to initiate cyclical replication in the asexual blood stage. The life-cycle is completed by the differentiation of a number of merozoites in the red blood cells into sexual stage gametocytes which are ingested by the mosquito, where they develop through a series of stages in the mid gut to produce sporozoites which migrate to the salivary gland.

Many countries have been experiencing resurgence in malaria cases caused by *Plasmodium falciparum* due to the spread of parasites which are increasingly resistant to both chloroquine, the drug most widely used for prevention and treatment as well as newer, alternative treatments such as artesunate. See, Wellems et al, JID 2001; 184 (15 September) and Noedl et al, N Engl J Med 2008; 359:2619-2620 (11 December). The development of new anti-malarial treatments is of great importance particularly given the rapid spread of parasite resistance even within newer artemisinin-based therapies.

In the battle against the continued spread of both malarial infection and the parasite resistance to malaria compounds having the potential to both combat the infection and also impact upon the parasite growth cycle, particularly against gametocyte development and thereby impacting upon subsequent transmission potential, would be highly desirable.

A further strand in assisting effective treatment of malarial infections is the need for therapies which can be dosed efficiently in difficult conditions. As such, single-dose, oral, rectal or parenteral therapies, particularly sustained or modified release therapies would be of value.

Thus there is a need for new and effective anti-malarial agents. In particular there is a need for new anti-malarial agents which: are effective against drug-resistant parasites; are effective against drug-resistant *Plasmodium falciparum* infections such as for example Chloroquine-resistant *Plasmodium falciparum* infections; which are active against gametocytes; have transmission-blocking potential; which are active against liver stage; which can be used for single-dose treatment; and/or which can be used for prophylactic treatment.

The present invention provides a novel class of class of quinolone-4-carboxamide compounds *Plasmodium falciparum* 3D7 inhibitors having potential as anti-malarial agents. The novel class of quinolone-4-carboxamide compounds according to the present invention have potential for the treatment of *Plasmodium falciparum, Plasmodium vivax, Plasmodium ovale, Plasmodium malariae* and *Plasmodium knowlesi* infections. In particular the novel class of class of quinolone-4-carboxamide compounds according to the present invention have potential for the treatment of *Plasmodium falciparum* infections; *Plasmodium falciparum* and *Plasmodium vivax* infections; *Plasmodium falciparum, Plasmodium vivax, Plasmodium ovale, Plasmodium malariae* and *Plasmodium knowlesi* infections.

Desirable properties of compounds of formula (I) according to the present invention include: potency against *Plasmodium falciparum* 3D7; low toxicity in MRC-5 or HepG2 cells; both desirable *Plasmodium falciparum* (Pf) 3D7 potency and low toxicity in MRC-5 or HepG2; desirable *Plasmodium falciparum* and *Plasmodium vivax* (Pv) activity against clinical isolates; desirable transmission blocking activity; gametocyte inhibitory potential; activity against dormant liver stage forms; good biopharmaceutical properties such as physical stability; good solubility profiles; appropriate metabolic stability; desirable ADME properties (adsorption, distribution, metabolism, excretion).

SUMMARY OF THE INVENTION

According to a first aspect the present invention provides compounds of formula (I)

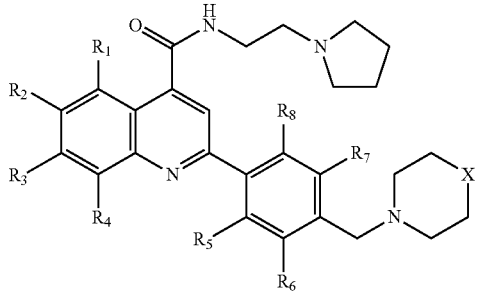

wherein $R^1$, $R^2$, $R^3$ $R^4$, $R^5$, $R^6$, $R^7$ and $R^8$ are independently of each other selected from: H, Cl or F; wherein the pyrrolidinyl, morpholinyl or thiomorpholinyl dioxide heterocyclic groups are independently optionally substituted by one or more Cl, F or —($C_1$-$C_3$)alkyl groups; and
wherein X is —O— or —$SO_2$—;
or a pharmaceutically acceptable salt, hydrate, solvate, isomer, prodrug or polymorph thereof.

The present invention additionally provides compounds of formula (I) wherein $R^1$, $R^2$, $R^3$ $R^4$, $R^5$, $R^6$, $R^7$ and $R^8$ are independently of each other selected from: H, Cl or F; wherein the pyrrolidinyl, morpholinyl or thiomorpholinyl dioxide heterocyclic groups are independently optionally substituted by one or more Cl, F or —($C_1$-$C_3$)alkyl groups; and
wherein X is —O— or —$SO_2$—; or a pharmaceutically acceptable salt, hydrate, solvate, isomer, prodrug or polymorph thereof.

According to a further aspect, the present invention provides compounds of formula (I) wherein X is —O—, compounds of formula (IA):

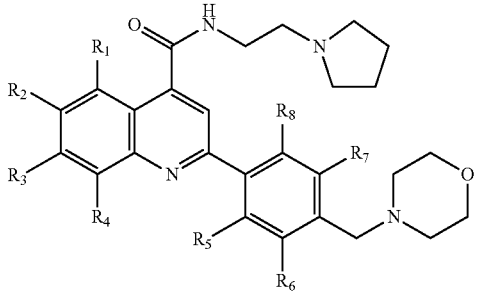

or a pharmaceutically acceptable salt, hydrate, solvate, isomer, prodrug or polymorph thereof
wherein $R^1$, $R^2$, $R^3$ $R^4$, $R^5$, $R^6$, $R^7$ and $R^8$ are independently of each other selected from: H, Cl or F; and wherein the pyrrolidinyl or morpholinyl groups are independently optionally substituted by one or more Cl, F or —($C_1$-$C_3$)alkyl groups.

In a yet further aspect, the present invention provides, compounds of formula (I) wherein X is —$SO_2$—, compounds of formula (IB):

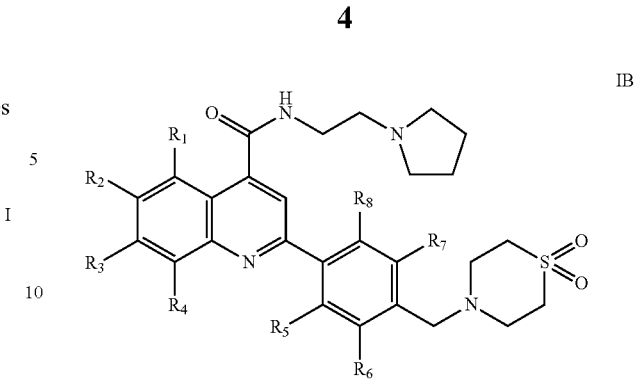

or a pharmaceutically acceptable salt, hydrate, solvate, isomer, prodrug or polymorph thereof
wherein $R^1$, $R^2$, $R^3$ $R^4$, $R^5$, $R^6$, $R^7$ and $R^8$ are independently of each other selected from: H, Cl or F; and wherein the pyrrolidinyl or thiomorpholinyl dioxide groups are independently optionally substituted by one or more Cl, F or —($C_1$-$C_3$)alkyl groups.

BRIEF DESCRIPTION OF THE DRAWINGS

Figure 1:
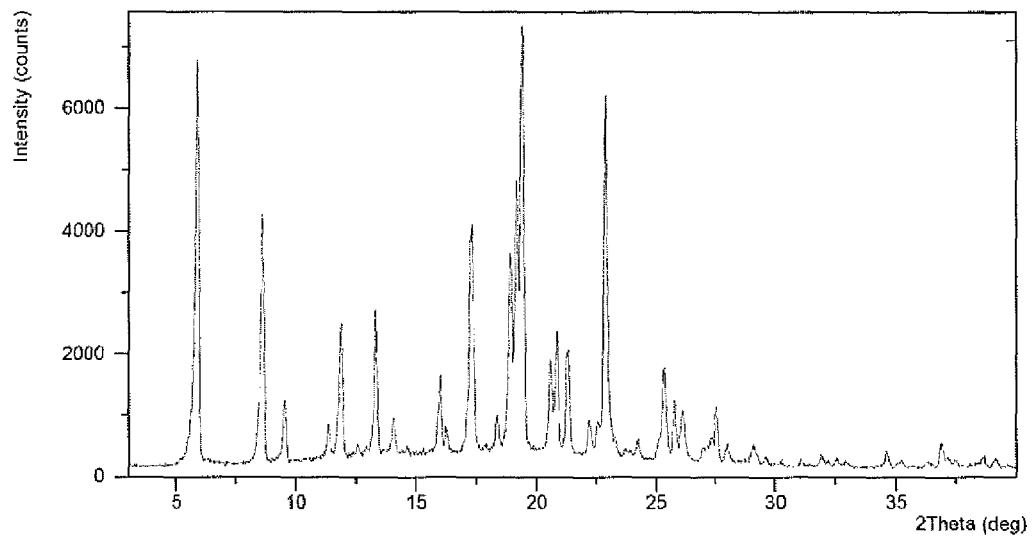

Having thus described the presently disclosed subject matter in general terms, reference will now be made to the accompanying Drawings, which are not necessarily drawn to scale, and wherein:

FIG. 1 is an X-ray powder diffraction pattern (XRPD) of a solid form of 6-Fluoro-2[4-(morpholinomethyl)phenyl]-N-(2-pyrrolidin-1-ylethyl)quinoline-4-carboxamide. The XRPD patterns illustrated in FIGS. 1 and 2 were analysed using a PANanalytical Empyrean XRPD on a Si single crystal holder and generated using CuKa1 and CuKa2 radiation, having wavelengths of 1.540598 Å and 1.544426 Å respectively, at a Ka2/Ka1 intensity ratio of 0.5.

Figure 2:
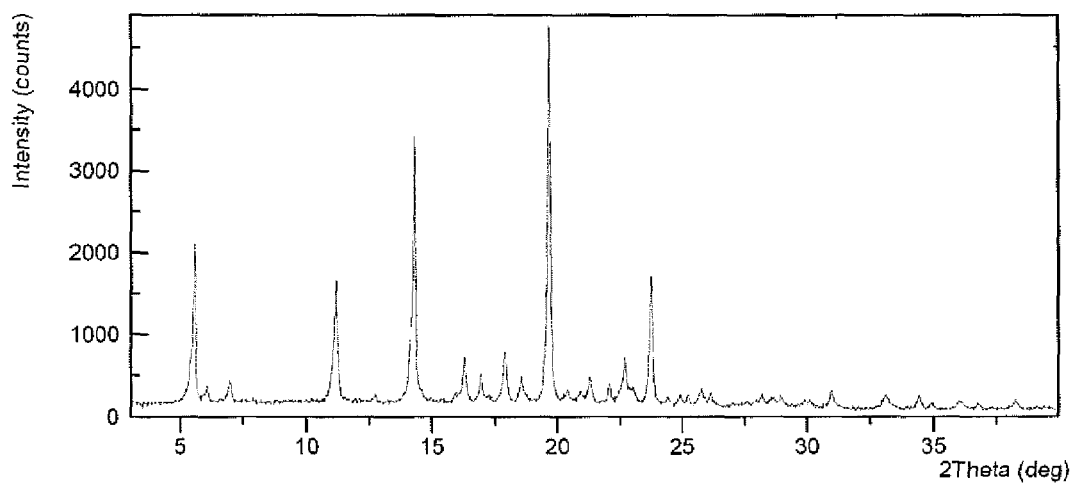

FIG. 2 is an X-ray powder diffraction pattern (XRPD) of a solid form of 6-Fluoro-2[4-(morpholinomethyl)phenyl]-N-(2-pyrrolidin-1-ylethyl)quinoline-4-carboxamide fumaric acid salt.

Figure 3:
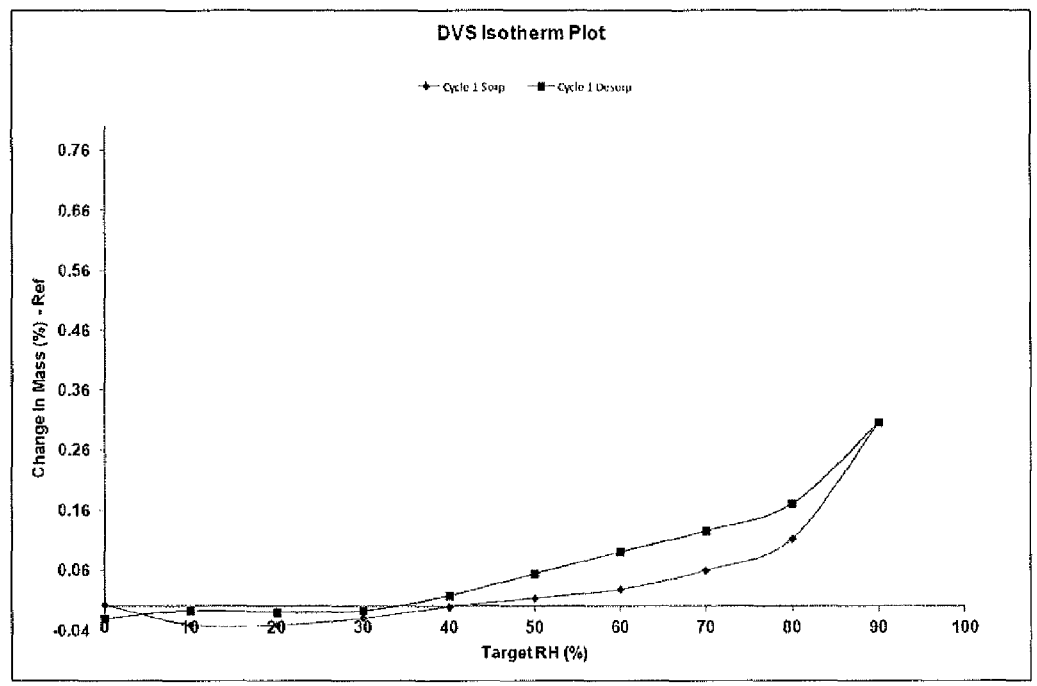
Figure 4:
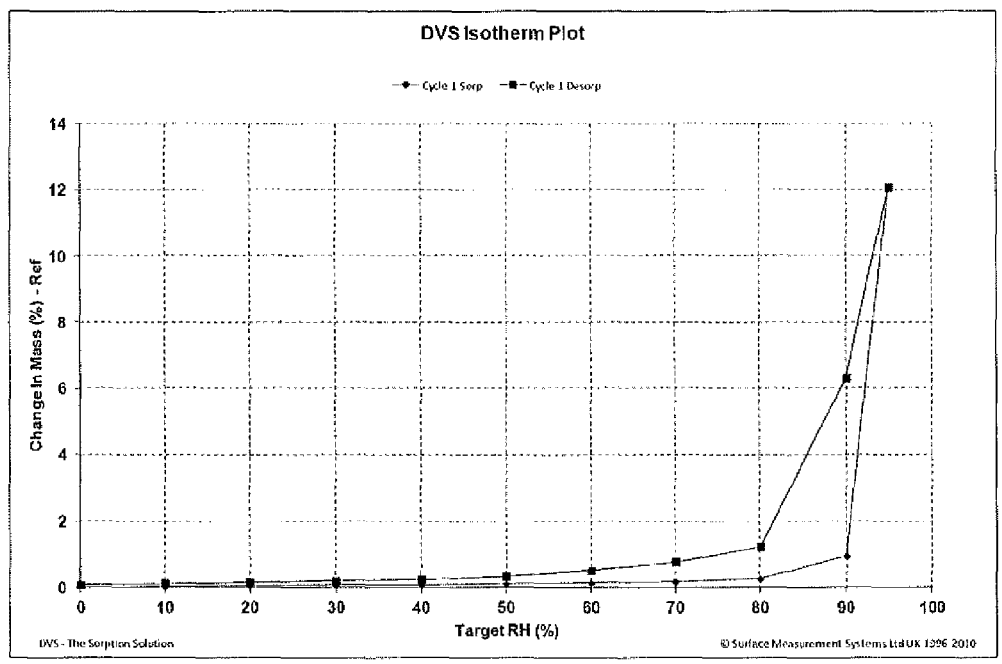

FIG. 3 is a dynamic vapour sorption (DVS) isotherm plot of the moisture sorption of Example 1A, 6-Fluoro-2[4-(morpholinomethyl)phenyl]-N-(2-pyrrolidin-1-ylethyl)quinoline-4-carboxamide. The DVS results illustrated in FIGS. 3 and 4 were measured using a SMS (Surface Measurement Systems) DVS Intrinsic and the relative humidity at 25° C. was calibrated against deliquescence point of LiCl , $Mg(NO_3)_2$ and KCl. The parameters for the DVS studies which generated FIGS. 3 and 4 are as listed in Table 4. The DVS results displayed in FIG. 3 shows a water uptake of 0.1% at 80% R.H./ 25° C.

FIG. 4 is a dynamic vapour sorption (DVS) isotherm plot of the moisture sorption of Example 2, 6-Fluoro-2-[4-(morpholinomethyl)phenyl]-N-(2-pyrrolidin-1-ylethyl)quinoline-4-carboxamide fumaric acid salt. The DVS results displayed in FIG. 4 shows a water uptake of 1.2% at 80% R.H./ 25° C.

Figure 5:
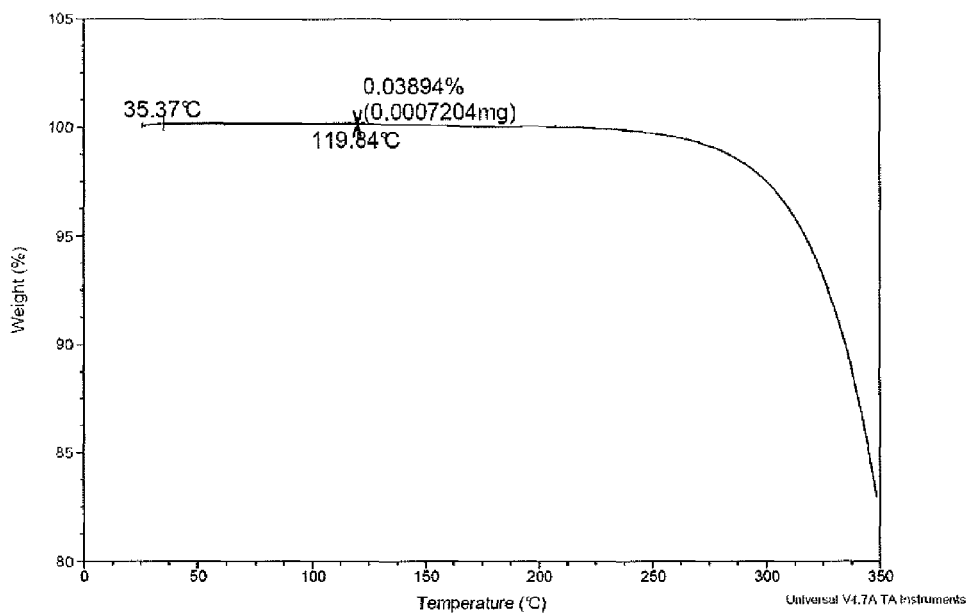
Figure 7:
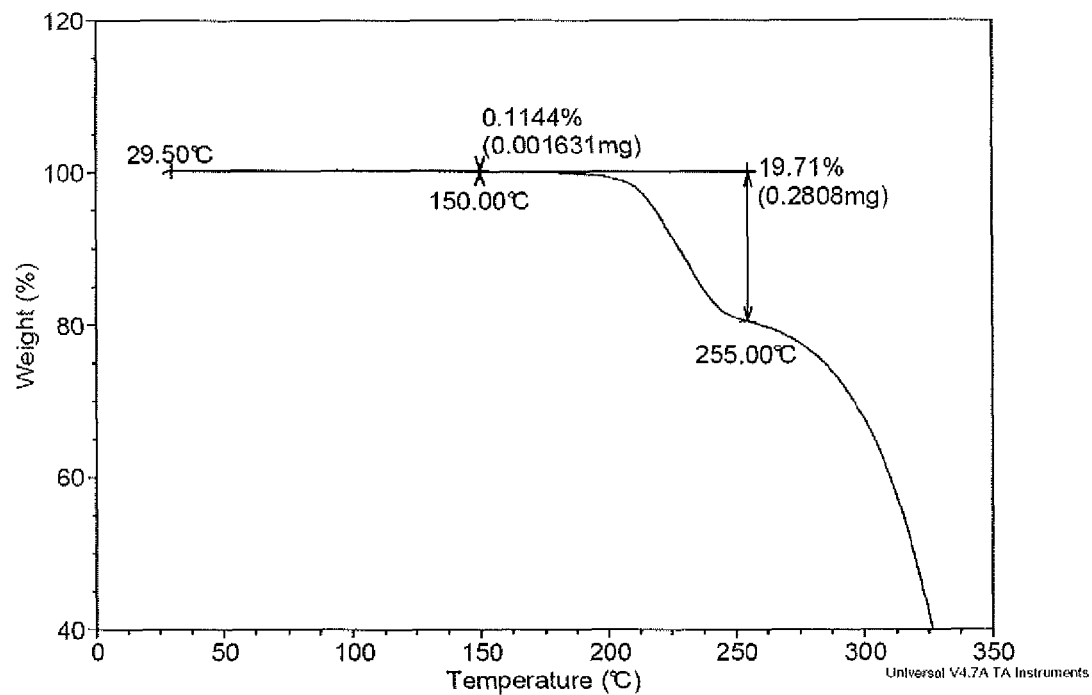

FIG. 5 illustrates the results of Thermogravimetric Analysis (TGA) of 6-Fluoro-2[4-(morpholinomethyl)phenyl]-N-(2-pyrrolidin-1-ylethyl)quinoline-4-carboxamide. The TGA results illustrated in FIGS. 5 and 7 show the changes in sample weight versus temperature and were conducted at 10° C./min ramping from 25° C. to 300° C. and carried out in open platinum pans using at TA Instruments Q5000 TGA. The remaining parameters for the TGA tests which generated FIGS. 5 and 7 are listed in Table 5. The TGA results displayed in FIG. 5 shows that negligible weight loss was observed upon heating up to ~120° C.

Figure 6:
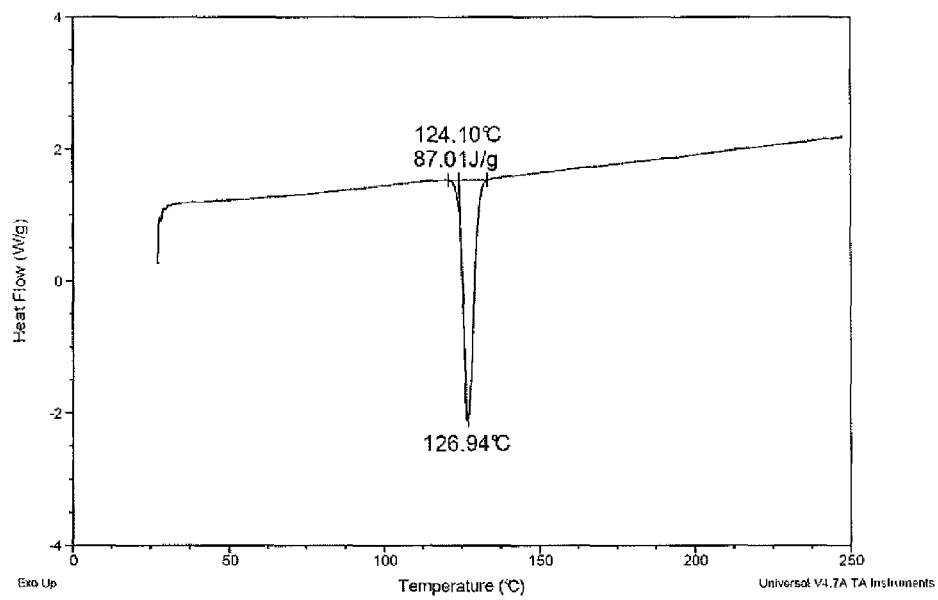
Figure 8:
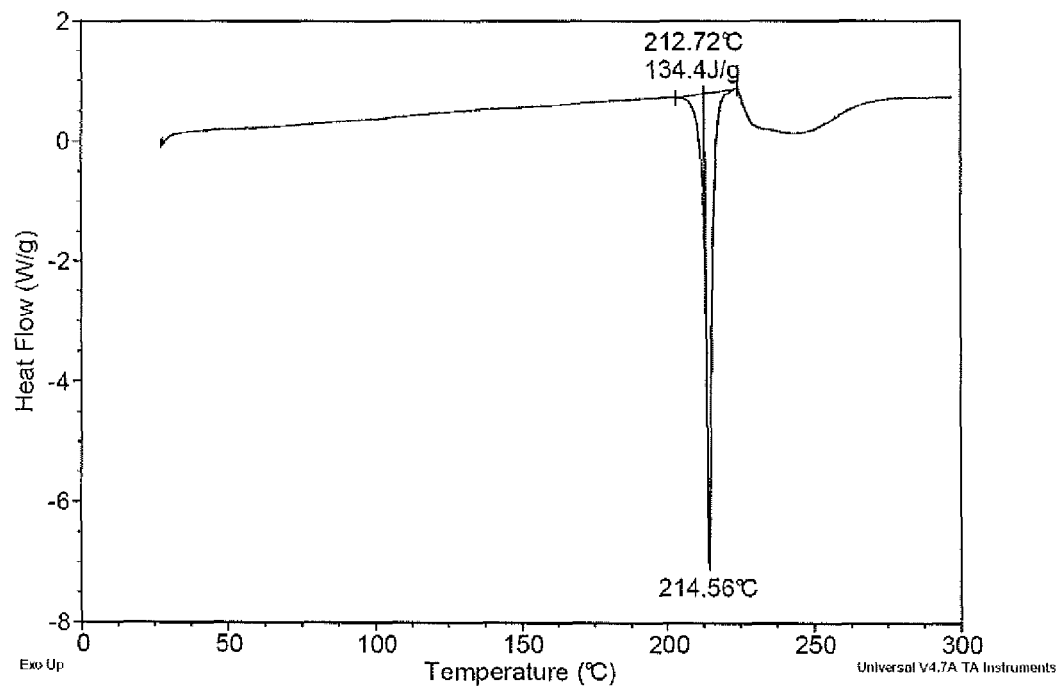

FIG. 6 illustrates the results of Differential scanning calorimetry (DSC) of 6-Fluoro-2-[4-(morpholinomethyl)phenyl]-N-(2-pyrrolidin-1-ylethyl)quinoline-4-carboxamide. The DSC results illustrated in FIGS. 6 and 8 show the changes in heat flow versus temperature and were conducted out in crimped aluminium pans using at TA Instruments Q2000 DSC. The parameters for the DSC studies which generated FIGS. 6 and 8 are as listed in Table 5. The DSC illustrated in FIG. 6 displays a single melting endotherm at 124.1° C., which is the onset temperature, and no additional events.

FIG. 7 illustrates the TGA results for 6-Fluoro-2[4-(morpholinomethyl)phenyl]-N-(2-pyrrolidin-1-ylethyl)quinoline-4-carboxamide fumaric acid salt. The TGA results displayed in FIG. 7 shows that negligible weight loss was observed upon heating up to ~150° C.

FIG. 8 illustrates the DSC results for 6-Fluoro-2[4-(morpholinomethyl)phenyl]-N-(2-pyrrolidin-1-ylethyl)quinoline-4-carboxamide fumaric acid salt. The DSC illustrated in FIG. 8 displays a single sharp melting endotherm at ~213° C. which is the onset temperature.

DESCRIPTION

For the avoidance of doubt, all definitions provided herein apply equally to general formula (I), (IA) and (IB) as detailed hereinbefore. As such, reference to compounds of formula (I) includes compounds of formula (IA) and (IB).

Scientific and technical terms used herein have the meanings with which they are commonly understood in the art unless specifically defined alternatively herein.

Where two or more moieties are described as being "each independently" selected from a list of atoms or groups, this means that the moieties may be the same or different. The identity of each moiety is therefore independent of the identities of the one or more other moieties.

In the above definitions, unless otherwise indicated, alkyl groups having two or more carbon atoms, may be unsaturated or saturated, and are preferably saturated; alkyl groups having three or more carbon atoms, may be straight chain or branched chain. For example, a $C_3$ alkyl substituent can be in the form of normal-propyl (n-propyl), or iso-propyl (i-propyl). For the avoidance of doubt where the pyrrolidine or morpholine group is optionally substituted by an alkyl group said alkyl group(s) may not be further substituted by a further (unsubstituted)alkyl group.

The term optionally substituted as used herein indicates that the particular group or groups may have one or more non-hydrogen substituents. The total number of such substituents which may be present is equal to the number of H atoms present on the unsubstituted form of the particular group. For example the pyrrolidinyl, morpholinyl and/or thiomorpholinyl dioxide groups in compounds of formula (I) may have one or two substituents. Preferably the pyrrolidinyl, morpholinyl and thiomorpholinyl dioxide groups in compounds of compounds of formula (I) are unsubstituted.

For the avoidance of doubt the term thiomorpholinyl dioxide as used herein includes the alternative terms 1,1-dioxothiomorpholinyl, 1,1-dioxo-thiomorpholinyl, thiomorpholinyl-1,1-oxide, thiomorpholinyl-1,1-dioxide, 1,1-dioxide-4-thiomorpholinyl; and 4-thiomorpholinyl-1,1-dione.

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

Compounds

The present invention provides compounds of formula (I):

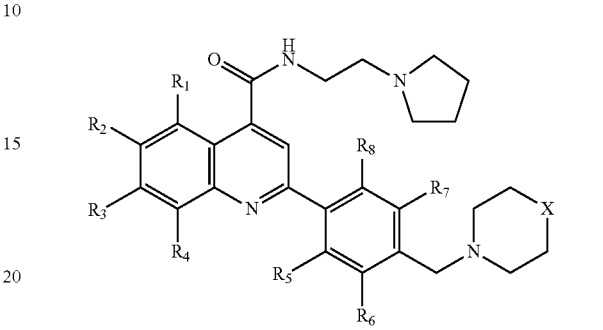

or a pharmaceutically acceptable salt, hydrate, solvate, isomer, prodrug or polymorph thereof
wherein $R^1$, $R^2$, $R^3$, $R^4$, $R^5$, $R^6$, $R^7$, $R^8$ and X are as defined hereinbefore.

Various embodiments of the invention, compounds of formula (I), are described below. The features specified in each embodiment may be combined with other specified features, from one or more other embodiments to provide further embodiments. For the avoidance of doubt, such further combined embodiments are embodiments of the present invention.

In an embodiment, $R^1$ is H or F. In an embodiment $R^1$ is H.

In an embodiment, $R^2$ is H or F. In an embodiment $R^2$ is F.

In a further embodiment $R^1$ and $R^2$ are independently selected from H or F. In a further embodiment, $R^1$ is H and $R^2$ is F.

In an embodiment, $R^2$ is H or Cl. In an embodiment $R^2$ is Cl. In a further embodiment $R^1$ is H and $R^2$ is Cl.

In an embodiment, $R^3$ and $R^4$ are each independently selected from H or F. In an embodiment, $R^3$ and $R^4$ are both H. In an embodiment $R^1$ and $R^2$ are independently selected from H or F, or from H or Cl, and $R^3$ and $R^4$ are each independently selected from H or F.

In an embodiment, the quinoline ring is mono- or di-substituted with F or Cl or a mixture thereof. In an embodiment, the quinoline ring is mono-substituted with a F or a Cl group.

In an embodiment $R^1$, $R^2$, $R^3$, and $R^4$ are each independently selected from H or F. In an embodiment $R^1$, $R^3$, and $R^4$ are H and $R^2$ is F.

In an embodiment, $R^5$, $R^6$, $R^7$, and $R^8$, are each independently selected from H or F.

In an embodiment, the phenyl ring is mono-, di- or tri-substituted with F or Cl or a mixture thereof. In an embodiment, the phenyl ring is mono-, di- or tri-substituted with F.

In an embodiment, the phenyl ring is mono-, di- or tri-substituted with Cl and $R^2$ is F or Cl.

In an embodiment, the phenyl ring is mono-, di- or tri-substituted with F and $R^2$ is F or Cl.

In an embodiment, $R^5$ and/or $R^8$ are each independently selected from H or F. In an embodiment, one of $R^5$ or $R^8$ is H and one of $R^5$ or $R^8$ is F.

In an embodiment, $R^6$ and/or $R^7$ are each independently selected from H or F. In an embodiment, one of $R^6$ or $R^7$ is H and one of $R^6$ or $R^7$ is F.

In an embodiment, $R^5$ and/or $R^6$ are each independently selected from H or F. In an embodiment, one of $R^5$ or $R^6$ is F.

In an embodiment, the phenyl ring is mono-substituted and wherein $R^5$ and/or $R^8$ are each independently selected from H or F.

In an embodiment, the phenyl ring is unsubstituted, $R^5$, $R^6$, $R^7$, and $R^8$ are all H. In an embodiment, the phenyl ring is unsubstituted and $R^2$ is F or Cl.

In an embodiment, the phenyl ring is unsubstituted, or mono-substituted by F and $R^2$ is F or Cl.

In an embodiment, $R^2$ is F and $R^5$ is H or F.

The following embodiments relate to compounds of the present invention, wherein X is —O—, having general formula (IA) wherein $R^1$, $R^2$, $R^3$, $R^4$, $R^5$, $R^6$, $R^7$, and $R^8$ are independently of each other selected from: H, Cl or F.

In an embodiment, $R^1$ is H or F. In an embodiment, $R^1$ is H.
In an embodiment, $R^2$ is H or F. In an embodiment, $R^2$ is F.
In a further embodiment, $R^1$ and $R^2$ are independently selected from H or F. In a further embodiment, $R^1$ is H and $R^2$ is F.

In an embodiment, $R^2$ is H or Cl. In an embodiment, $R^2$ is Cl. In a further embodiment, $R^1$ is H and $R^2$ is Cl.

In an embodiment, $R^3$ and $R^4$ are each independently selected from H or F. In an embodiment, $R^3$ and $R^4$ are both H.

In an embodiment, the quinoline ring is mono- or di-substituted with F or Cl or a mixture thereof. In an embodiment, the quinoline ring is mono-substituted with a F or a Cl group.

In an embodiment, $R^1$, $R^2$, $R^3$, and $R^4$ are each independently selected from H or F. In an embodiment, $R^1$, $R^3$, and $R^4$ are H and $R^2$ is F.

In an embodiment, $R^5$, $R^6$, $R^7$, and $R^8$, are each independently selected from H or F.

In an embodiment, the phenyl ring is mono-, di- or tri-substituted with F or Cl or a mixture thereof. In an embodiment, the phenyl ring is mono-, di- or tri-substituted with F.

In an embodiment, the phenyl ring is mono-, di- or tri-substituted with F and $R^2$ is F or Cl.

In an embodiment, the phenyl ring is mono-, di- or tri-substituted with Cl and $R^2$ is F or Cl.

In an embodiment, $R^5$ and/or $R^8$ are each independently selected from H or F. In an embodiment, one of $R^5$ or $R^8$ is H and one of $R^5$ or $R^8$ is F.

In an embodiment, $R^6$ and/or $R^7$ are each independently selected from H or F. In an embodiment, one of $R^6$ or $R^7$ is H and one of $R^6$ or $R^7$ is F.

In an embodiment, $R^5$ and/or $R^6$ are each independently selected from H or F. In an embodiment, one of $R^5$ or $R^6$ is F.

In an embodiment, the phenyl ring is mono-substituted and wherein $R^5$ and/or $R^8$ are each independently selected from H or F.

In an embodiment, the phenyl ring is unsubstituted, $R^5$, $R^6$, $R^7$, and $R^8$ are all H. In an embodiment, the phenyl ring is unsubstituted and $R^2$ is F or Cl.

In an embodiment, the phenyl ring is unsubstituted, or mono-substituted by F and $R^2$ is F or Cl.

In an embodiment, $R^2$ is F and $R^5$ is H or F.

In an embodiment, $R^3$, $R^4$, $R^6$, $R^7$ and $R^8$ are each independently selected from H or F.

The following embodiments relate to compounds of the present invention, wherein X is —SO$_2$—, having general formula (IB) wherein $R^1$, $R^2$, $R^3$, $R^4$, $R^5$, $R^6$, $R^7$, and $R^8$ are independently of each other selected from: H, Cl or F.

In an embodiment, $R^1$ and $R^2$ are independently selected from H or F. In a further embodiment, $R^1$ is H and $R^2$ is F.

In an embodiment, the quinoline ring is mono- or di-substituted with F or Cl or a mixture thereof. In an embodiment, the quinoline ring is mono-substituted with a F or a Cl group.

In an embodiment, $R^1$, $R^2$, $R^3$, and $R^4$ are each independently selected from H or F. In an embodiment, $R^1$, $R^3$, and $R^4$ are H and $R^2$ is F.

In an embodiment, $R^5$, $R^6$, $R^7$, and $R^8$, are each independently selected from H or F.

In an embodiment, the phenyl ring is unsubstituted. In an embodiment, the phenyl ring is unsubstituted and $R^2$ is F or Cl. In an embodiment, the phenyl ring is unsubstituted, or mono-substituted by F and $R^2$ is F or Cl.

Preferred compounds according to the present invention wherein X is —O— or —SO$_2$—; $R^1$, $R^3$, $R^4$, $R^6$ and $R^7$ are H; $R^2$ is F; and $R^5$ and $R^8$ are independently selected from H or F include the compounds of examples 1 to 11 and pharmaceutically acceptable salts, solvates and hydrates thereof.

Particularly preferred individual compounds according to the present invention include:
6-Fluoro-2-[4-(morpholinomethyl)phenyl]-N-(2-pyrrolidin-1-ylethyl)quinoline-4-carboxamide;
6-Fluoro-2-[4-(morpholinomethyl)phenyl]-N-(2-pyrrolidin-1-ylethyl)quinoline-4-carboxamide fumaric acid salt;
6-chloro-2-[4-(morpholinomethyl)phenyl]-N-(2-pyrrolidin-1-ylethyl)quinoline-4-carboxamide;
2-[4-(morpholinomethyl)phenyl]-N-(2-pyrrolidin-1-ylethyl)quinoline-4-carboxamide;
6-fluoro-2-(3-fluoro-4-(morpholinomethyl)phenyl)-N-(2-(pyrrolidin-1-yl)ethyl)quinoline-4-carboxamide;
2-[4-(morpholinomethyl)phenyl]-N-(2-pyrrolidin-1-ylethyl)quinoline-4-carboxamide fumaric acid salt;
6-fluoro-2-(2-fluoro-4-(morpholinomethyl)phenyl)-N-(2-(pyrrolidin-1-yl)ethyl)quinoline-4-carboxamide;
2-(3,5-difluoro-4-(morpholinomethyl)phenyl)-6-fluoro-N-(2-(pyrrolidin-1-yl)ethyl)quinoline-4-carboxamide;
2-(4-((1,1-dioxidothiomorpholino)methyl)phenyl)-6-fluoro-N-(2-(pyrrolidin-1-yl)ethyl)quinoline-4-carboxamide;
2-(2,6-difluoro-4-(morpholinomethyl)phenyl-6-fluoro-N-(2-(pyrrolidin-1-yl)ethyl)quinoline-4-carboxamide;
2-(2,3-difluoro-4-(morpholinomethyl)phenyl)-6-fluoro-N-(2-(pyrrolidin-1-yl)ethyl)quinoline-4-carboxamide;
2-(2-chloro-4-(morpholinomethyl)phenyl)-6-fluoro-N-(2-(pyrrolidin-1-yl)ethyl)quinoline-4-carboxamide;
2-(2-chloro-4-(morpholinomethyl)phenyl)-6-fluoro-N-(2-(pyrrolidin-1-yl)ethyl)quinoline-4-carboxamide fumaric acid salt;

and pharmaceutically acceptable acid salts, hydrates, solvates, isomers, pro-drugs or polymorphs thereof and for the avoidance of doubt, where said compounds are listed as salts, then alternative pharmaceutically acceptable acid salts, hydrates, solvates, isomers, pro-drugs or polymorphs thereof are considered to be included.

Highly preferred individual compounds according to the present invention are:
6-Fluoro-2-[4-(morpholinomethyl)phenyl]-N-(2-pyrrolidin-1-ylethyl)quinoline-4-carboxamide;
6-Fluoro-2-[4-(morpholinomethyl)phenyl]-N-(2-pyrrolidin-1-ylethyl)quinoline-4-carboxamide fumaric acid salt; and
6-Fluoro-2-(2-fluoro-4-(morpholinomethyl)phenyl)-N-(2-(pyrrolidin-1-yl)ethyl)quinoline-4-carboxamide.
6-Fluoro-2-[4-(morpholinomethyl)phenyl]-N-(2-pyrrolidin-1-ylethyl)quinoline-4-carboxamide is especially preferred.

Pharmaceutically acceptable acid addition salts of certain compounds of the formula (I) may be readily prepared in a conventional manner by mixing together solutions of a compound of the formula (I) and the desired acid, as appropriate. For example, a solution of the free base is treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties Selection, and Use" by Stahl and Wermuth (Wiley-VCH, Weinheim, Germany, 2002). Suitable acid addition salts for use herein include: fumarate, acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, and trifluoroacetate.

The compounds of the invention may exist in a continuum of solid states ranging from fully amorphous to fully crystalline. The compounds of the invention may also exist in unsolvated and solvated forms. The term 'solvate' as used herein describes a molecular complex comprising the compound of the invention and one or more pharmaceutically acceptable solvent molecules, for example, ethanol. The term 'hydrate' is employed when said solvent is water. Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. For a general review of multi-component complexes, see J Pharm Sci, 64 (8), 1269-1288, by Haleblian (August 1975). Hereinafter all references to compounds of formula (I) include references to salts, solvates, and multi-component complexes.

The compounds of the invention include compounds of formula (I) as hereinbefore defined, and polymorphs and crystal habits thereof.

Isomers of compounds of formula (I) as used herein, and included in the present invention include optical, geometric and tautomeric isomers. Stereoisomers such as enantiomers and diastereomers, all geometric isomers and tautomeric forms of the compounds of formula (I), including compounds exhibiting more than one type of isomerism, and mixtures of one or more thereof are included in the present invention. Also included are acid addition salts wherein the counterion is optically active, for example, d-lactate or l-lysine, or racemic, for example, dl-tartrate or dl-arginine. Geometric isomers may be separated by conventional techniques well known to those skilled in the art, for example, by chromatography and fractional crystallisation. Stereoisomers may be separated by conventional techniques known to those skilled in the art—see, for example, "Stereochemistry of Organic Compounds" by E L Eliel (Wiley, New York, 1994).

As indicated, so-called 'prodrugs' of the present compounds are also within the scope of the invention. Thus certain derivatives of compounds of formula (I), which may have little or no pharmacological activity themselves, can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T Higuchi and W Stella) and *Bioreversible Carriers in Drug Design*, Pergamon Press, 1987 (Ed. E B Roche, American Pharmaceutical Association). Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H Bundgaard (Elsevier, 1985). Finally, certain compounds of formula (I) may themselves act as prodrugs of other compounds of formula (I).

Also included within the scope of the invention are metabolites of compounds of formula I, that is, compounds formed in vivo upon administration of the drug. An example of a metabolite in accordance with the invention is a phenol derivative of a compound of formula I (-Ph->-PhOH).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature. Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

It is to be appreciated that references to treatment as used herein includes prophylaxis as well as palliative treatment via the alleviation of established symptoms of a condition i.e. prevention or control. "Treating" or "treatment" of a state, disorder or condition includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

Prophylactic treatment of malaria as defined herein included includes the treatment of a subject with a prophylaxis-effective amount of compound of formula (I) wherein said prophylaxis-effective amount is an amount of compound that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites Treatment of malaria as defined herein includes: treatment of *Plasmodium falciparum, Plasmodium vivax, Plasmodium ovale, Plasmodium malariae* and/or *Plasmodium knowlesi* infections; treatment of *Plasmodium falciparum* infections; treatment of *Plasmodium falciparum* and *Plasmodium vivax* infections; treatment of *Plasmodium falciparum, Plasmodium vivax, Plasmodium ovale, Plasmodium malariae* and *Plasmodium knowlesi* infections; treatment of the latent forms of vivax malaria.

Regarding the use of the compounds of the invention in humans, there is provided:

a pharmaceutical composition comprising a compound of formula (I), or a pharmaceutically acceptable salt, solvate, hydrate, isomer, prodrug or polymorph thereof, together with one or more pharmaceutically acceptable carrier, diluent or excipient;

a compound of formula (I), or a pharmaceutically acceptable salt, solvate, hydrate, isomer, prodrug or polymorph thereof, or a pharmaceutical composition containing any of the foregoing, for use as a medicament;

a compound of formula (I), or a pharmaceutically acceptable salt, solvate, hydrate, isomer, prodrug or polymorph thereof, or a pharmaceutical composition containing any of the foregoing, for use in the prophylactic treatment of malaria;

a compound of formula (I), or a pharmaceutically acceptable salt, solvate, hydrate, isomer, prodrug or polymorph thereof, or a pharmaceutical composition containing any of the foregoing, for use in the treatment of malaria;

use of compound of formula (I), or a pharmaceutically acceptable salt, solvate, hydrate, isomer, prodrug or polymorph thereof for the preparation of a pharmaceutical formulation for the treatment of malaria;

a compound of formula (I), or a pharmaceutically acceptable salt, solvate, hydrate, isomer, prodrug or polymorph thereof, or a pharmaceutical composition containing any of the foregoing, for use in the treatment of drug-resistant malaria;

Regarding the use of the compounds of the invention in animals, there is provided:

a veterinary composition comprising a compound of formula (I), or an acceptable salt, solvate, hydrate, isomer, prodrug or polymorph thereof, together with one or more acceptable carrier, diluent or excipient;

a compound of formula (I), or an acceptable salt, solvate, hydrate, isomer, prodrug or polymorph thereof, or a veterinary composition containing any of the foregoing, for use as a veterinary medicine.

Further diseases, disorders or conditions affecting humans or animals which may be treatable with the compounds of the present invention include, but are not limited to: *pneumocystis carinii; eimeria*; and/or conditions related to Apicomplexa parasites having apicoplastis causing diseases such as toxoplasmosis, coccidiosis, cryptosporidiosis, babesiosis, theileriosis, cyclosporiasis, sarcocysticosis and isosporiasis; and/or neosporosis, caused by the apicomplexan parasite *Neospora caninum*.

Process for Preparation

The following routes illustrate methods of synthesising compounds of formula (I) and (IA). Scheme 1 illustrates a general route of the preparation of the quinolone-4-carboxamide compounds of formula (I) via Suzuki coupling of intermediates (II) and (III). The quinoline amide intermediate (III) is prepared from the corresponding acid (IV) in a two-stage synthesis, firstly one pot generation of an acid chloride and chlorination of the quinolone ring at C-2, followed by conversion to the desired amide via treatment with 2-pyrrolidin-1-ylethanamine. Acid intermediate (IV) is prepared from a suitable isatin via treatment with malonic acid and acetic acid. The boronic ester intermediate (II) is prepared from the corresponding 4-bromophenyl compound (V) via treatment with 4,4,5,5,-tetramethyl-2-(4,4,5,5-tetramethyl-1,3,2-dioxaborolan-2-yl)-1,3,2-dioxaborolane in a palladium catalysed coupling. In the route shown removal of traces of palladium via a metal scavenger is performed prior to optional conversion of one compound of formula (I) to its corresponding fumarate salt (I).

SCHEME 1

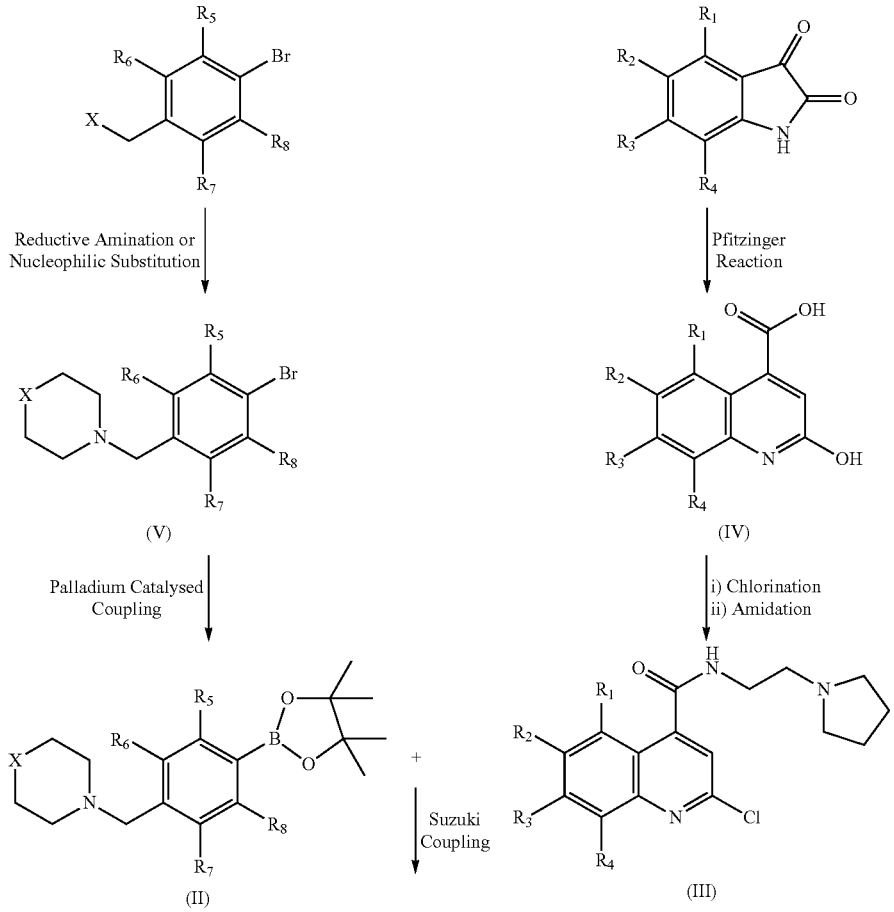

-continued

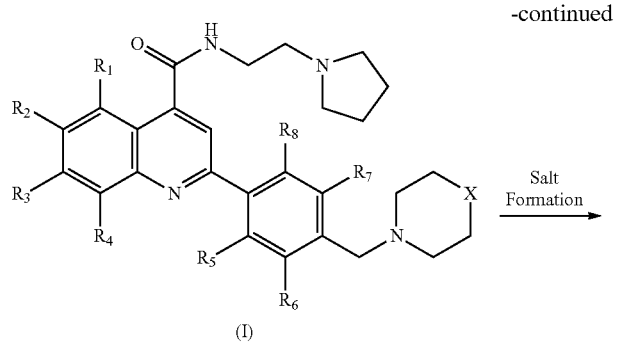

(I)

X = Br, = O

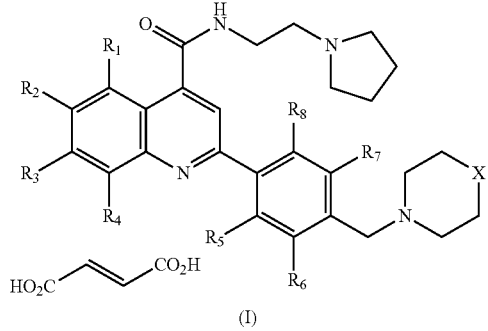

(I)

In respect of compounds (I), (II), (III), (IV) and (V) in Scheme 1 the definitions of X, $R^1$, $R^2$, $R^3$, $R^4$, $R^5$, $R^6$, $R^7$ and $R^8$ are as defined hereinbefore for compounds of formula (I) unless stated otherwise.

Thus according to a further embodiment the present invention provides a process for the preparation of quinoline-4-carboxamide compounds of general formula (I) comprising Suzuki coupling of a boronic ester of general formula (II) with a quinoline amide of general formula (III).

In a preferred group of compounds according to the present invention X is —O—. Thus according to a further embodiment the present invention provides a general process for the preparation of quinoline-4-carboxamide compounds wherein X is —O— of general formula (IA) comprising Suzuki coupling of a boronic ester of general formula (II) wherein X is —O— with a quinoline amide of general formula (III).

Scheme 2 illustrates suitable reagents and reaction conditions for the preparation of the compound of Example 1 hereinafter. As will be appreciated by the skilled chemist the reagents and conditions employed in the transformations in Scheme 2 may be utilised, modified and/or substituted for alternatives as necessary in order to furnish various alternative compounds via the general processes in Scheme 1.

SCHEME 2

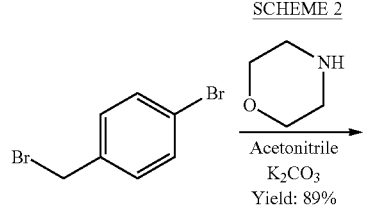

Acetonitrile
$K_2CO_3$
Yield: 89%

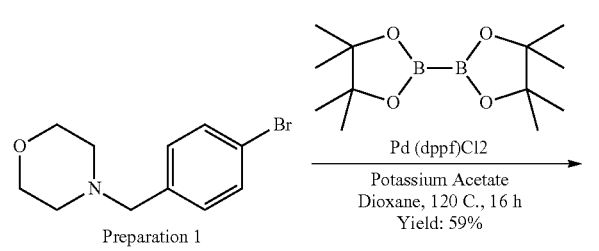

Pd (dppf)Cl2
Potassium Acetate
Dioxane, 120 C., 16 h
Yield: 59%

Preparation 1

-continued

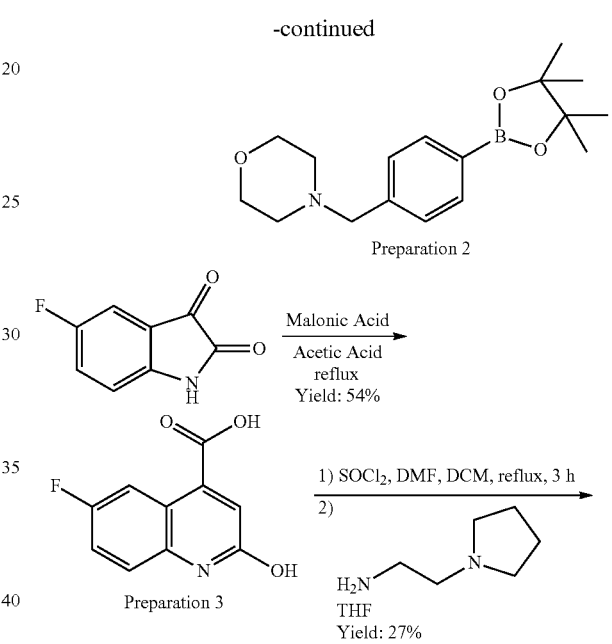

Preparation 2

Malonic Acid
Acetic Acid
reflux
Yield: 54%

Preparation 3

1) SOCl₂, DMF, DCM, reflux, 3 h
2)

THF
Yield: 27%

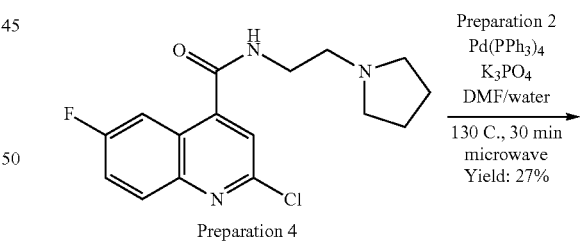

Preparation 4

Preparation 2
Pd(PPh₃)₄
K₃PO₄
DMF/water

130 C., 30 min
microwave
Yield: 27%

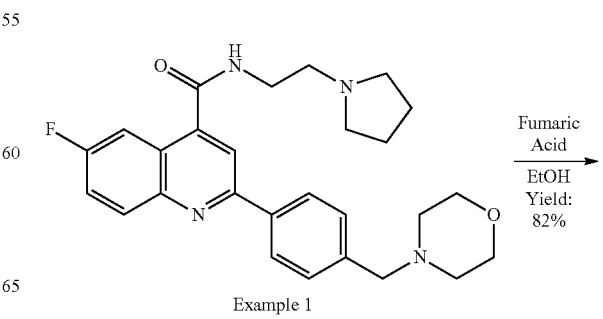

Example 1

Fumaric Acid
EtOH
Yield: 82%

-continued

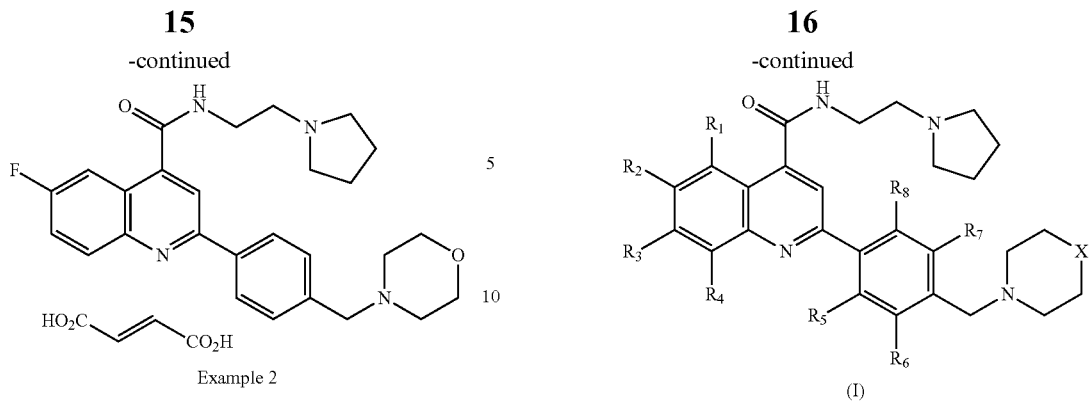

Example 2

Thus according to a further embodiment the present invention provides a process for the preparation of the compound of Example 1 comprising Suzuki coupling of the relevant boronic ester compound (preparation 2) and quinoline amide compound (preparation 4).

According to a yet further embodiment the present invention provides the intermediate compound of preparation 4.

Scheme 3 illustrates an alternative route for the preparation of the compounds of general formula (I).

SCHEME 3

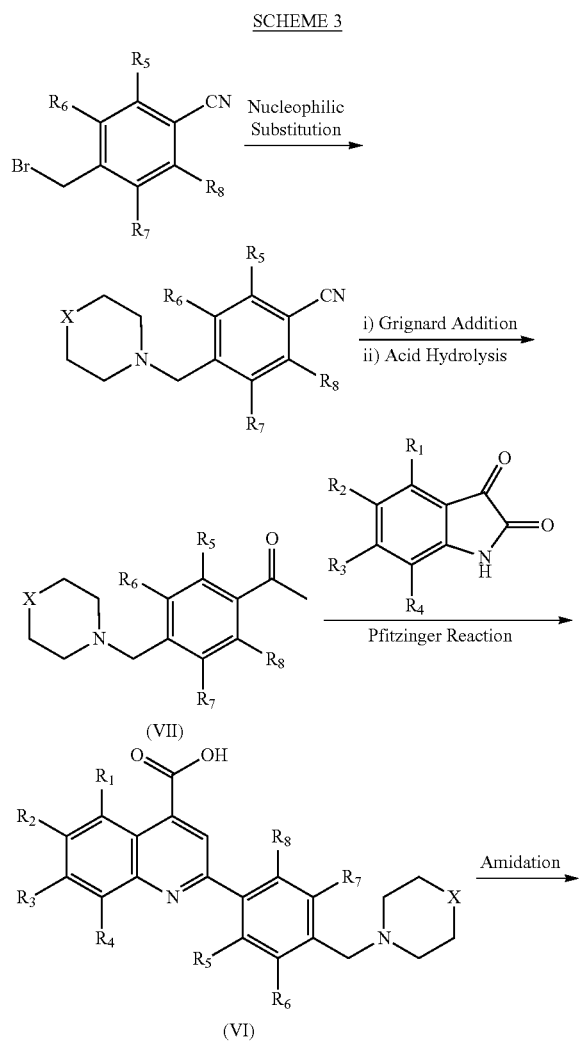

In respect of compounds (I), (VI) and (VII) in Scheme 3 the definitions of X, $R^1$, $R^2$, $R^3$, $R^4$, $R^5$, $R^6$, $R^7$ and $R^8$ are as defined hereinbefore for compounds of formula (I) unless stated otherwise.

In Scheme 3 the quinolin-4-carboamides of formula (I) can be provided either via direct coupling of phenylquinoline-4-carboxylic acid intermediate (VI) with the corresponding amine or alternatively via initial formation of the corresponding acid chloride followed by amine addition. Acid intermediate (VI) can be prepared by reaction of the corresponding ethanone (VII) with the desired isatin either using microwave irradiation or conventional heating.

Scheme 4 illustrates suitable reagents and reaction conditions for an alternative preparation of the compound of Example 1 via the general processes in Scheme 3. This route is employed in the synthesis of Example 1A hereinafter. As will be appreciated by the skilled chemist the reagents and conditions employed in the transformations in Scheme 4 may be utilised, modified and/or substituted for alternatives as necessary in order to furnish various alternative compounds via the general processes in Scheme 3.

SCHEME 4

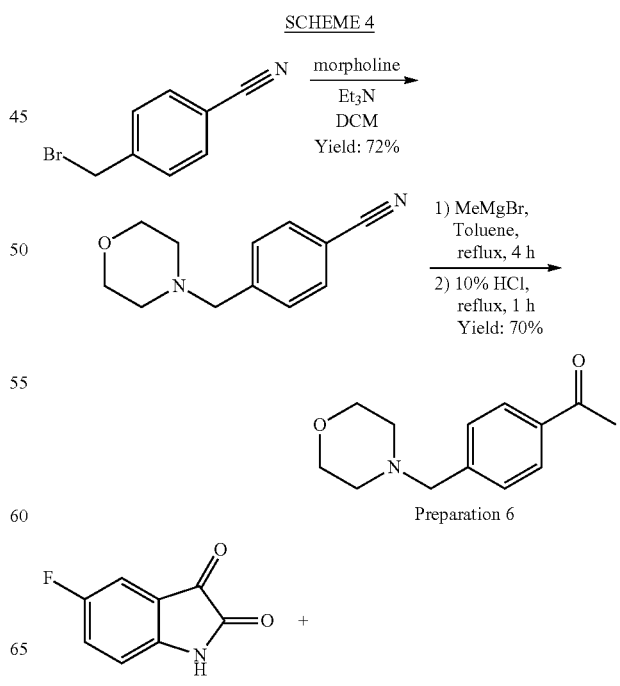

-continued

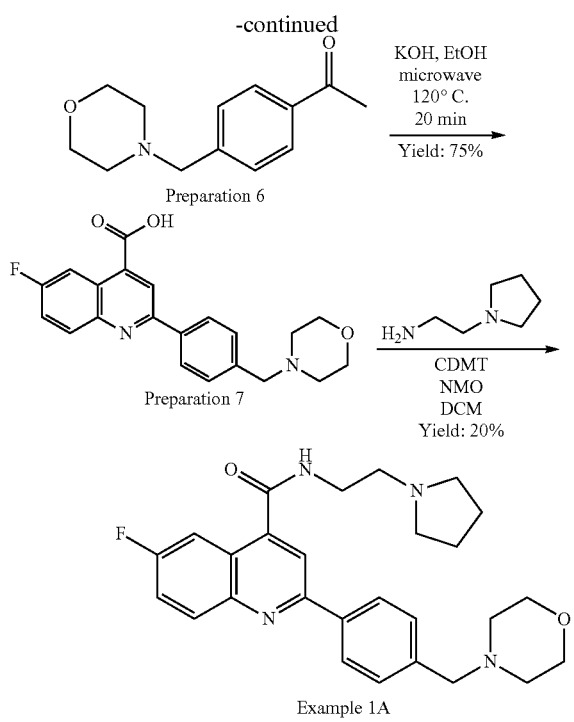

Preparation 6

Preparation 7

Example 1A

Thus according to a further embodiment the present invention provides a process for the preparation of the compound of Example 1A comprising coupling of the phenylquinoline-4-carboxylic acid intermediate of preparation 7 with 2-(pyrrolidin-1-yl)ethanamine.

According to a yet further embodiment the present invention provides a process for the preparation of the intermediate compound of preparation 7 comprising coupling of the 1-[4-(morpholinomethyl)phenyl]ethanone intermediate compound of preparation 6 with isatin.

The general reaction mechanisms described hereinbefore for the preparation of novel starting materials used in the preceding methods are conventional and appropriate reagents and reaction conditions for their performance or preparation as well as procedures for isolating the desired products will be well-known to those skilled in the art with reference to literature precedents and the Examples and Preparations hereto.

It will also be appreciated by a person skilled in the art that the compounds of the invention could be made by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

It will also be apparent to a person skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

According to an embodiment the present invention provides processes for the preparation of compounds of general formula (I) using analogous methods to those provided for the preparation of the compound of Example 1 via preparations 1, 2, 3, and 4.

According to a preferred embodiment the present invention provides processes for the preparation of compounds of general formula (I) using analogous methods to those provided for the preparation of the compound of Example 1A via preparations 6 and 7.

The compounds of the present invention may be delivered in combination with one or more auxiliary active agents for the treatment of malaria. Suitable auxiliary active agents for use in the combinations of the present invention include: Artemisinin and derivatives thereof such as for example Artesunate; Quinine and related agents; Chloroquine; OZ439; NITD609; ferroquine; napthoquine; piperaquine; Pyrimethamine; Proguanil; Sulphonamide based therapies; Mefloquine, including Mefloquine hydrochloride; Atovaquone; Primaquine; Halofantrine; Doxycyline; Clindamycin; Amodiaquine, marketed as Camoquin, or Flavoquine; and/or Aertemether, including the combination with lumefantrine available from Novartis as Riamet and Coartem.

The suitability of a potential combination of two, or more, antimalarial drugs can be assessed on the basis of their in vitro drug interactions wherein the interactions of the two selected antimalarial drugs are investigated in vitro using standard dose-response assays over a range of individualised concentrations. The selection of suitable conditions and concentrations for carrying out such investigations would be within the remit of the skilled practitioner.

According to a further aspect the present invention provides a pharmaceutical composition comprising: a compound of formula (I) or a pharmaceutically acceptable, salt, solvate, hydrate, isomer, prodrug, or polymorph thereof; one or more additional antimalarial agents; and one or more pharmaceutically acceptable carriers, diluents or excipients.

Examples of suitable combinations herein include a compound of the present invention and one or more additional therapeutic agents selected from: artesunate; mefloquine; OZ439, piperaquine and mixtures thereof.

If a combination of active agents is administered, then the composition comprising a compound of formula (I) as detailed hereinbefore may be administered to an individual prior to, simultaneously, separately or sequentially with other therapeutic regiments or co-agents useful in the treatment of malaria. If a combination of active agents is administered, then the different actives may be formulated for the same or different delivery, for example one active formulated for immediate and another for sustained release. If a combined therapy is to be administered the active agents may be formulated for the same or different routes of administration, for example in a dual-therapy one active may be formulated for oral administration and another for parenteral administration.

Administration and Dose Ranges

In order to select the most appropriate dosage forms and routes of administration considered appropriate for the treatment of the desired indication, compounds of formula (I) should be assessed for their biopharmaceutical properties, such as for example, solubility, solution stability (across a range of pHs), likely dose level and permeability. Initial biopharmaceutical testing for potential as anti-malarial treatment has provided positive results.

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form. Pharmaceutically acceptable excipients include one or more of: lubricants, binding agents, diluents, surface-active agents, anti-oxidants, colorants, flavouring agents, preservatives, flavour enhancers, preservatives, salivary stimulating agents, cooling agents, co-solvents (including oils), emollients, bulking agents, anti-foaming agents, surfactants and taste-masking agents.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Formulations suitable for oral administration include solids, semi-solids or liquids such as tablets; soft or hard capsules; bolus; powders; lozenges (including liquid-filled); chews; multi and nano-particulates; gels; solid solutions; fast-dispersing dosage forms; fast-dissolving dosage forms; fast-disintegrating dosage forms; films; ovules; sprays; buccal/mucoadhesive patches; and liquid formulations. Liquid formulations include suspensions, solutions, elixirs and syrups. Oral administration may involve swallowing, so that the compound enters the gastrointestinal tract, and/or buccal, lingual or sublingual administration by which the compound enters the blood stream directly from the mouth. Liquid formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Formulations for oral administration may be formulated to be immediate and/or modified release. Modified release formulations include delayed-, sustained-, pulsed-, controlled-, targeted and programmed release. The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The present invention provides a pharmaceutical composition formulated for oral delivery comprising a compound of formula (I) or a pharmaceutically acceptable, salt, solvate or hydrate thereof, according to any preceding claim, together with one or more pharmaceutically acceptable excipients. The present invention further provides said pharmaceutical composition formulated for oral delivery as an immediate release, or as a modified release tablet formulation.

The compounds of the invention may also be administered parenterally, or by injection directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

The present invention provides a pharmaceutical composition formulated for parenteral delivery comprising a compound of formula (I) or a pharmaceutically acceptable, salt, solvate or hydrate thereof, according to any preceding claim, together with one or more pharmaceutically acceptable excipients. The present invention further provides said pharmaceutical composition formulated for parenteral delivery as an immediate release, or as a modified release tablet formulation suitable for intramuscular or intravenous administration.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used.

The compounds of the invention may be administered rectally or vaginally, for example, in the form of a suppository, pessary, or enema. Cocoa butter is a traditional suppository base, but various alternatives may be used as appropriate.

Pharmaceutical formulations containing compounds of the invention may be formulated to be immediate and/or modified release. Modified release formulations include delayed-, sustained-, pulsed-, controlled-, targeted and programmed release.

Dosages

Typically, a physician will determine the actual dosage which will be most suitable for an individual subject. The specific dose level and frequency of dosage for any particular individual may be varied and will depend upon a variety of factors including the condition being treated, the activity of the specific compound employed, the metabolic stability and length of action of that compound, the age, body weight, general health, sex, diet, mode and time of administration, rate of excretion, drug combination, the severity of the particular condition, and the individual undergoing therapy.

In general however a suitable dose will be in the range of from about 0.001 to about 50 mg/kg of body weight per day, in a further embodiment, of from about 0.001 to about 5 mg/kg of body weight per day; in a further embodiment of from about 0.001 to about 0.5 mg/kg of body weight per day and in yet a further embodiment of from about 0.001 to about 0.1 mg/kg of body weight per day. In further embodiments, the ranges can be of from about 0.001 to about 750 mg/kg of body weight per day, in the range of 0.5 to 60 mg/kg/day, and in the range of 1 to 20 mg/kg/day.

The desired dose may conveniently be presented in a single dose or as divided doses administered at appropriate intervals, for example as one, two, three, four or more doses per day. If the compounds are administered transdermally or in extended release form the compounds could be dosed once a day or less.

The compound is conveniently administered in unit dosage form; for example containing 0.1 to 50 mg, conveniently 0.1 to 10 mg, most conveniently 0.1 to 5 mg of active ingredient per unit dosage form. In yet a further embodiment the compound can be conveniently administered in unit dosage form; for example containing 10 to 1500 mg, 20 to 1000 mg, or 50 to 700 mg of active ingredient per unit dosage form.

These dosages are based on an average human subject having a weight of about 65 kg to 70 kg. The physician will readily be able to determine doses for subjects whose weight falls outside this range, such as infants and the elderly.

The present invention provides a pharmaceutical composition formulated as a single-dose tablet suitable for oral delivery comprising a compound of formula (I) or a pharmaceutically acceptable, salt, solvate or hydrate thereof, together with one or more pharmaceutically acceptable excipients. The present invention further provides said pharmaceutical composition formulated for oral delivery as an immediate release, or as a modified release single-dose tablet formulation.

The present invention further provides a pharmaceutical composition formulated as a single-dose tablet formulated for oral delivery as an immediate release, or as a modified release single-dose tablet formulation comprising from about 0.1 to about 3000 mg, preferably from about 0.5 to about 1500 mg, more preferably from about 1 to about 750 mg, from about 1 to about 750 mg, and especially from about 5 to about 250 mg of a compound of formula (I) or a pharmaceutically acceptable, salt, solvate or hydrate thereof, together with one or more pharmaceutically acceptable excipients.

For anti-malarial treatment a single-dose treatment is highly desirable to increase effective treatment levels; increase compliance rates; as well as to reduce treatment costs.

For anti-malarial treatment the present invention further provides a pharmaceutical composition formulated as a single-dose tablet formulated for oral delivery as an immediate release, or as a modified release single-dose tablet formulation comprising from 0.1 to 3000 mg, preferably from about 0.5 to about 1500 mg, more preferably from about 1 to about 750 mg and especially from about 5 to about 250 mg of a compound of formula (I) or a pharmaceutically acceptable, salt, solvate or hydrate thereof, together with one or more pharmaceutically acceptable excipients.

Where single treatment therapy via a large dose is to be administered, for example to a child, the dose could be provided by more than one tablet, such as 2×1500 mg, or 3×1000 mg, rather than a single-dose 3000 mg tablet where the tablets may be taken either one after the other, or together according to suitability.

Inasmuch as it may desirable to administer a combination of active compounds, as detailed hereinbefore, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

For the avoidance of doubt, references herein to "treatment" include references to curative, palliative and prophylactic treatment.

Malaria

Compounds of the present invention are useful in the treatment of malaria. Compounds according to the present invention have potential for the treatment of *Plasmodium falciparum*, *Plasmodium vivax*, *Plasmodium ovale*, *Plasmodium malariae* and *Plasmodium knowlesi* infections. In particular the novel class of class of quinolone-4-carboxamide compounds according to the present invention have potential for the treatment of *Plasmodium falciparum* infections; *Plasmodium falciparum* and *Plasmodium vivax* infections; *Plasmodium falciparum*, *Plasmodium vivax*, *Plasmodium malariae*, *Plasmodium ovale* and *Plasmodium knowlesi* infections.

In particular the novel class of class of quinolone-4-carboxamide compounds according to the present invention have potential for the treatment of malaria attributable to infection from the life-threatening form of malaria attributable to *Plasmodium falciparum*.

Malaria is caused by an infection of the red blood cells with a tiny organism or parasite called protozoa. Infection of the five species of the malaria protozoa, *Plasmodium falciparum*, *Plasmodium vivax*, *Plasmodium ovale*, *Plasmodium malariae* and *Plasmodium knowlesi* occurs through the injection of protozoa into the blood stream, is effected by a single source, the bite of the female *Anopheles* mosquito.

*Plasmodium* species, requires two hosts, human and mosquito for completion of its life-cycle. In humans the infection is initiated by the inoculation of sporozoites in the saliva of an infected mosquito. Once inside the body the sporozoites migrate to the liver and there infect hepatocytes where they differentiate, via the exoerythrocytic intracellular stage, into the merozoite stage which infects red blood cells to initiate cyclical replication in the asexual blood stage. The life-cycle is completed by the differentiation of a number of merozoites in the red blood cells into sexual stage gametocytes which are ingested by the mosquito, where they develop through a series of stages in the mid gut to produce sporozoites which migrate to the salivary gland. According to a further aspect the present invention provides compounds of formula (I) for use as anti-malarial medicaments.

Compounds of the invention have been demonstrated to display both functional in vitro potency against a malarial *Plasmodium* strain and desirable in vivo potency in a *Plasmodium* mouse model.

*Plasmodium falciparum* In vitro Screening and Results

Compounds of general formula (I) according to the present invention have been shown to have desirable inhibitory activity, expressed as an $EC_{50}$, against *Plasmodium falciparum* strain 3D7, Pf 3D7. The experimental methods and some results are provided hereinafter.

Parasite cultures and cytotoxicity assay methodology for *Plasmodium falciparum*. Cultures of the widely-used malaria reference strain of chloroquinine-sensitive *Plasmodium falciparum* strain 3D7 were maintained in a 5% suspension of human red blood cells cultured in RPMI 1640 medium supplemented with 0.5% Albumax II (available from Gibco Life Technologies, San Diego, Calif.), 12 mM sodium bicarbonate, 0.2 mM hypoxanthine, (pH 7.3), and 20 mg/litre gentamicin at 37° C., in an atmosphere of 1% $O_2$, 3% $CO_2$ with a gas balance of nitrogen. Growth inhibition of the *Plasmodium falciparum* cultures was quantified using a fluorescence assay utilising the binding of SYBRgreen to double stranded DNA, which greatly increased the fluorescent signal at 528 nm after excitation at 485 nm. Mefloquine was used as a drug control to monitor the quality of the assay (Z'=0.6 to 0.8, where Z' is a measure of the discrimination between the positive and negative controls on a screen plate). Dose-response curves were determined from a minimum of 3 independent experiments. Compound bioactivity was expressed as $EC_{50}$, the effective concentration of compound causing 50% parasite death.

Quinoline-4-carboxamide compounds of formula (I) exhibited desirable activity profiles against Pf 3D7. Table 1 illustrates the relative bioactivity of compounds of formula (I) against Pf 3D7.

TABLE 1

| Example | EC$_{50}$ (µM) for Pf 3D7 |
|---------|---------------------------|
| 1 | 0.001 |
| 2 | 0.007 |
| 3 | 0.001 |
| 4 | 0.001 |
| 5 | 0.003 |
| 6 | 0.0007 |
| 7 | 0.0005 |
| 8 | 0.004 |
| 9 | 0.0006 |
| 11 | 0.003 |

Preferably the present compounds exhibit a functional potency against Pf 3D7 expressed as an EC$_{50}$, less than about 0.1 micromolar (µM), more preferably lower than about 0.05 micromolar (µM), yet more preferably lower than about 0.01 micromolar (µM), more preferably still lower than about 0.005 micromolar (µM), and especially about 0.001 micromolar (µM) or less, wherein said EC$_{50}$ measurement of Pf 3D7 functional potency can be carried out using the methodology described hereinbefore. Compounds according to the present invention, including compounds of the Examples 1 to 11, have been tested and found to demonstrate functional potencies of less than about 0.007 micromolar (µM).

Thus according to a further embodiment the present invention provides compounds of formula (I) having a functional potency against Pf 3D7 of less than about 0.1 micromolar (µM), preferably less than about 0.05, more preferably less than about 0.01, and particularly about 0.001 micromolar (µM) or less against Pf 3D7.

Transmission Blocking Properties

In addition to the present need for new drugs with desirable anti-malarial activity, compounds which also either inhibit or kill the sexual stages of *Plasmodium* species i.e. the gametocytes have the potential to block transmission to mosquitoes. Gametocytes represent a vital link in human/vector malaria transmission as this is the only stage in the malaria parasite life-cycle capable of infecting mosquitoes. Transmission blocking pathways include: inhibition of metabolic processes in early gametocytogenesis; toxicity against mature gametocytes; and inhibition or disruption of gametogenesis and/or sporogony. In the continued effort to reduce/eliminate the spread of malaria drugs having such gametocyticidal and/or sporontocidal properties, would provide a significant new dimension to existing treatments, either as a sole medicament having both anti-malarial and transmission blocking properties, or as a complementary therapy with alternative anti-malarial drugs for a transmission blocking therapy.

Transmission blocking properties are based on a compounds effect on the gametocyte stage of the parasite and can be assessed using a number of literature procedures such as for example Malaria Journal, 2012, 11, 34 the contents of which are incorporated herein by reference. Additionally, there are published biological assays for in vitro testing against mosquito stages of the malaria parasite like male gamete production (exflagelation) and ookinate development, for example the procedure described in PLOS Medicine, 2012, 9, e1001169, the contents of which are incorporated by reference.

Initial testing indicates that compounds of the invention are effective transmission blockers against the gametocyte stage IV and V of the *Plasmodium falciparum* parasite, male gamete production (exflagellation) in *Plasmodium falciparum* and ookinete development in *Plasmodium berghei*.

Thus, according to a further aspect the present invention provides compounds of formula (I) for use as a transmission blocking medicament.

Activity Against *Plasmodium* Liver Stage

A further need for new drugs with anti-malarial activity is for compounds that can cure the parasite stages in the liver protecting from infection and eliminating dormant parasites (hypnozoites) form of *Plasmodium vivax* and *Plasmodium ovale*. This stage remains dormant for a significant period of time (months or even years) after an initial infection and can be re-activated without a mosquito bite and give rise to a new episode of malaria. New drugs which completely clear this dormant liver stage are urgently needed. The activity of compounds of the invention against *Plasmodium yoelli* liver stage can be assessed using literature procedures such as for example, PLOS Medicine, 2012, 9, e1001169, page 4, the contents of which are incorporated by reference. Additionally, dormant liver stages can be assessed using literature procedures such as for example PLOS One, 2011, 6, e18162.

Initial testing indicates that compounds of the invention are effective against liver stage of *Plasmodium yoelli*. According to a further aspect the present invention provides compounds of formula (I) having potential for use as in latent liver stage medicaments.

A further need for new drugs with anti-malarial activity is for compounds which can treat malaria with a single administration of compound. An object of the invention is to provide compounds having potential for use in single dose treatments for malaria.

A further need for new drugs with anti-malarial activity is for compounds which are active against drug-resistant malaria strains. Drug resistance to malaria is a major problem. There is a need for new classes of compound which are active against drug resistant strains of malaria found in the field. Preliminary testing has demonstrated activity of a compound of formula (I) against a Chloroquine resistant strain of malaria. According to a further aspect the present invention provides compounds of formula (I) for use in the treatment of drug-resistant malaria.

Anti-malarial In vivo Data

*Plasmodium* species that lead to human malarial infection are essentially unable to infect non-primate animal models. Rodent models as antimalarial drug discovery efficacy models for compound screening have been extensively used and validated for use through the identification of several antimalarial drugs such as mefloquine, and artemisinin derivatives. Such mouse models, including the *Plasmodium berghei* mouse model are an integral part of the drug discovery and development pathway. In vivo data for the potential anti-malarial efficacy of compounds of general formula (I) has been demonstrated using the *Plasmodium berghei* mouse model of the disease. In particular experimental results have shown that a compound of formula (I) has improved potency, expressed as ED$_{90}$, the dose required to eradicate 90% of the target infection [ED$_{90}$ of 0.3-0.1 mg/kg], versus existing anti-malarial drugs.

Methodology. Using the standard Peter's test in NMRI female mice infected with GFP-transfected *Plasmodium berghei* ANKA strain were used. Test compounds were dosed orally once a day for four days at nine dose levels (0.003, 0.001, 0.03, 0.1, 0.3, 1, 3, 10, 30 mg/kg) and parasitaemia assessed 24 h after the last dose to determine ED$_{90}$. The test protocol is described in detail Nature, 2004, 430, 900-904, the contents of which are included herein by reference.

Quinoline-4-carboxamide compounds of formula (I) exhibited desirable in vivo behaviour in the *P. berghei* mouse model. Preliminary results indicate that compounds of the invention have desirable levels of efficacy in this model versus current antimalarial therapies. Compounds of formula (I) have been demonstrated to have comparable or improved potency than current antimalarial therapies.

The results shown in Table 2 demonstrate the oral efficacy of compounds of the invention in this mouse model.

TABLE 2

| Example | Dose mg/kg 4x | % Reduction in parasitaemia | Mean Survival (days) |
|---|---|---|---|
| 1 | 1 | 99.9 | 14 |
| 6 | 1 | 99.8 | 11 |
| 7 | 1 | 99.9 | 11 |
| 9 | 1 | 99.0 | 7 |

Compounds identified as being active in such four-day assays can subsequently be progressed through several secondary tests as follows. In the 'dose ranging, full four-day test', compounds are tested at a minimum of four different doses, by subcutaneous and/or oral routes, to determine $ED_{50}$ and $ED_{90}$ values. This test also provides useful information on relative potency and oral bioavailability. In the 'onset/recrudescence' test, mice are administered a single dose (by subcutaneous or oral route) on day 3 post-infection and followed daily to monitor parasitaemia. Results are expressed as the rapidity of onset of activity (disappearance of parasitaemia), time to onset of recrudescence, increase of parasitaemia and survival in number of days. Compounds can also be tested for prophylactic activity by administering the compound prior to infection, followed by daily examination of smears.

Compounds can be further assessed using a murine model of *Plasmodium falciparum* malaria (the so-called *P. falciparum* SCID mouse model). The murine *Plasmodium falciparum* models require the engrafment of mice with human erythrocytes. The use NODscidIL2Rγ$^{null}$ mice engrafted with human erythrocytes and competent *P. falciparum* strains have been validated for the preclinincal evaluation of antimalarials. The test protocol is described in detail at Antimicrobial Agents and Chemotherapy, 2009, 53 4533-4536, the contents of which are included herein by reference.

Quinoline-4-carboxamide compounds of formula (I), and in particular the compound of Example 1A, exhibited desirable in vivo behaviour in the *P. falciparum* SCID mouse model. Preliminary results indicate that compounds of the invention have desirable levels of efficacy in this model versus current antimalarial therapies. Compounds of formula (I) have been demonstrated to have comparable or improved potency than current antimalarial therapies.

The standard membrane feeding assay (SMFA) is used to test the potential effects of compounds or drugs on sporogonic development in the mosquito and it is used to asses their potential for malaria transmission blocking in vivo. The test protocol is described in detail at Antimicrobial Agents and Chemotherapy, 2012, 56 3544-3548 and PLoS ONE 7(8): e42821, the contents of which are included herein by reference.

Quinoline-4-carboxamide compounds of formula (I), and in particular the compound of Example 1A, exhibited desirable in vivo behaviour in standard membrane feeding assay. Preliminary results indicate that compounds of the invention have desirable levels of efficacy in this model versus current antimalarial therapies. Compounds of formula (I) have been demonstrated improved potency than current antimalarial therapies.

Compounds can be also tested for transmission blocking potential in a mouse to mouse transmission blocking assay.

Cytotoxicity Studies

In-vitro cytotoxicity studies can be carried out using either MRC-5 (human diploid embryonic lung cell, HPACC cat. no. 05090501) or Hep G2 (Human Caucasian hepatocyte carcinoma, HPACC cat. no. 85011430) used as indicators for general mammalian cell toxicity.

Initial results obtained using the MRC5 in-vitro cytotoxicity assay methodology as described in ChemMedChem 2011, 6, 1832-1840 the contents of which are incorporated herein by reference, indicate that compounds of the present invention have desirable cytotoxicity for MRC-5 cells.

Quinoline-4-carboxamide compounds of formula (I) exhibited desirable cytotoxicity behaviour for MRC-5 cells when screened at 10 different concentrations within a concentration range of from 50 μM to 2.5 nM. Preferred compounds of formula (I) have a relative selectivity for Pf 3D7 compare with mammalian cells of more than 100 fold.

Thus according to a further aspect the present invention provides compounds of formula (I) having desirable Pf 3D7 potency and low cytotoxicity in MRC-5, and in particular compounds having a functional potency against Pf 3D7 of less than about 0.1 micromolar (μM) and a relative cytotoxicity for MRC-5 expressed as $EC_{50}$, of about 22 μM or more. According to a yet further aspect the present invention provides compounds of formula (I) having desirable Pf 3D7 potency and low cytotoxicity in MRC-5, and in particular compounds having a functional potency against Pf 3D7 of less than about 0.007, preferably less than about 0.005, and especially about 0.001 or less micromolar (μM) and a relative selectivity compared to mammalian cells of more than 100 fold, preferably of more than 500 fold, more preferably more than 1000 fold.

Hep G2 in-vitro cytotoxicity can be assessed using the assay procedure as described in "Use of a human-derived liver cell line for the detection of cytoprotective, antigenotoxic and cogenotoxic agents", Volker Mersch-Sundermann, Siegfried Knasmüller, Xin-jiang Wu, Firouz Darroudi, Fekadu Kassie. *J. Tox* 198 (2004) 329-340) the contents of which are incorporated herein by reference.

X-Ray Powder Diffraction (XRPD) Pattern

Compounds of the invention have been analysed by XRPD using a PANanalytical Empyrean XRPD on a Si single crystal holder. The 20 position was calibrated against PANanalytical 640 Si podwer standard. Details of the XRPD method used in the experiments are listed below.

TABLE 3

| Typical XRPD parameters | |
|---|---|
| Reflection mode | |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 2°-40° |
| Step size (°2TH) | 0.0170 |
| Scan speed (°/min) | About 10 |

The XRPD patterns of example 1A and example 2 are illustrated in FIGS. 1 and 2 respectively and indicate both samples are highly crystalline with no evidence of amorphous content.

Thus the present invention additionally provides a solid form of 6-Fluoro-2-[4-(morpholinomethyl)phenyl]-N-(2-pyrrolidin-1-ylethyl)quinoline-4-carboxamide having an X-ray powder diffraction pattern (XRPD) with main peaks substantially as illustrated in FIG. 1 wherein said XRPD pattern was generated using CuKα1 and CuKα2 radiation, having wavelengths of 1.540598 Å and 1.544426 Å respectively, at a Kα2/Kα1 intensity ratio of 0.5.

The present invention also additionally provides a solid form of 6-Fluoro-2-[4-(morpholinomethyl)phenyl]-N-(2-pyrrolidin-1-ylethyl)quinoline-4-carboxamide fumaric acid salt having an X-ray powder diffraction pattern (XRPD) with main peaks substantially as illustrated in FIG. 2 wherein said XRPD pattern was generated using CuKα1 and CuKα2 radiation, having wavelengths of 1.540598 Å and 1.544426 Å respectively, at a Kα2/Kα1 intensity ratio of 0.5".

Dynamic Vapor Sorption (DVS)

The moisture sorption of compounds of the invention was measured using a SMS (Surface Measurement Systems) DVS Intrinsic. The relative humidity at 25° C. was calibrated against deliquescence point of LiCl, Mg(NO$_3$)$_2$ and KCl. Parameters for DVS test are listed below.

TABLE 4

Parameters for DVS test

| | DVS |
|---|---|
| Temperature | 25° C. |
| Sample size | 10-20 mg |
| Gas and flow rate | N$_2$, 200 ml/min |
| dm/dt | 0.002%/min |
| Min · dm/dt stability duration | 10 min |
| Max. equilibrium time | 180 min |
| RH range | 95% RH-0% RH-95% RH |
| RH step size | 10%(90% RH-0% RH-90% RH) |
| | 5%(95% RH-90% RH and 90% RH-95% RH) |

DVS data for example 1A, as displayed in FIG. 3 shows a water uptake of 0.1% at 80% R.H./25° C., indicating this compound is non-hygroscopic. No solid form change was observed post DVS testing.

DVS data at 25° C. for example 2 displayed in FIG. 4 suggests this fumarate salt is slightly hygroscopic with water uptake of ~1.2% at 80% R.H. No solid form change was observed post DVS testing.

TGA and DSC Analysis

Thermogravimetric Analysis (TGA) of compounds of the invention was conducted at 10° C./min ramping form room temperature to desired temperature in open platinum pans using at TA Instruments Q5000 TGA. The temperature was calibrated using nickel and weight using TA-supplied standard weights and verified against calcium oxalate monohydrate dehydration and decomposition. Typical parameters for TGA are described in Table 5.

Differential scanning calorimetry (DSC) was performed on compounds of the invention was performed with a TA instrument Q2000 DSC in crimped aluminium pan. The temperature and heat flow were calibrated against indium melting. Typical parameters for DSC are listed in Table 5.

TABLE 5

TGA and DCS parameters

| | TGA | DSC |
|---|---|---|
| Temperature | 25° C.-300° C. | 25° C.-300° C. |
| Ramp rate | 10° C./min | 10° C./min |
| Purge gas | N$_2$ | N$_2$ |
| Pan type | Platinum, open | Aluminum, crimped |

TGA data for example 1A displayed in FIG. 5 shows that negligible weight loss (<0.1 wt %) was observed upon heating to ~120° C. The DSC (FIG. 6) displays a single melting endotherm at 124.1° C. (onset temperature). No additional events were witnessed in the DSC suggesting example 1A is single phase with no evidence of polymorph transitions upon heating.

TGA data for example 2 displayed in FIG. 7 shows that negligible weight loss was observed upon heating to ~150° C. The DSC (FIG. 8) displays a single sharp melting endotherm at ~213° C. (onset temperature).

The invention is illustrated by the following non-limiting examples in which the following abbreviations and definitions are used:

Abbreviations

APCI atmospheric pressure chemical ionisation mass spectrum
δ chemical shift
d Doublet
dd double doublet
DCM Dichloromethane
DMF Dimethylformamide
ES low resolution electro spray mass spectroscopy
EtOAc Ethyl acetate
HPLC high performance liquid chromatography
HRMS high resolution mass spectrum
LCMS liquid chromatography mass spectrometry
m Multiplet
min Minutes
m/z mass spectrum peak
NMR nuclear magnetic resonance
q Quartet
rt room temperature
S Singlet
T Triplet
THF Tetrahydrofuran
TLC thin layer chromatography Equipment Reactions using microwave irradiation were carried out in a Biotage Initiator microwave. Normal phase TLCs were carried out on pre-coated silica plates (Kieselgel 60 F$_{254}$, BDH) with visualisation via U.V. light (UV254/365 nm) and/or ninhydrin solution. Flash chromatography was performed using Combiflash Companion Rf (Teledyne ISCO) and prepacked silica gel columns purchased from Grace Davison Discovery Science or SiliCycle. Mass-directed preparative HPLC separations were performed using a Waters HPLC (2545 binary gradient pumps, 515 HPLC make up pump, 2767 sample manager) connected to a Waters 2998 photodiode array and a Waters 3100 mass detector. Preparative HPLC separations were performed with a Gilson HPLC (321 pumps, 819 injection module, 215 liquid handler/injector) connected to a Gilson 155 UV/vis detector. On both interments, HPLC chromatographic separations were conducted using Waters XBridge C18 columns, 19×100 mm, 5 um particle size; using 0.1% ammonia in water (solvent A) and acetonitrile (solvent B) as mobile phase. $^1$H NMR, $^{19}$F NMR spectra were recorded on a Bruker Avance DPX 500 spectrometer ($^1$H at 500.1 MHz, $^{13}$C at 125 MHz $^{19}$F at 470.5 MHz), or a Bruker Avance DPX 300 ($^1$H at 300 MHz). Chemical shifts (δ) are expressed in ppm recorded using the residual solvent as the internal reference in all cases. Signal splitting patterns are described as singlet (s), doublet (d), triplet (t), quartet (q), multiplet (m), broad (br), or a combination thereof. Coupling constants (J) are quoted to the nearest 0.5 Hz. Low resolution electrospray (ES) mass spectra were recorded on a Bruker MicroTof mass spectrometer, run in positive mode. High resolution mass spectroscopy (HRMS) was performed using a Bruker MicroTof mass spectrometer. LC-MS analysis and chromatographic separation were conducted with a Brucker MicrOTOf mass spectrometer or an Agilent Technologies 1200 series HPLC connected to an Agilent Technologies 6130 quadrupole LC/MS, where both instruments were connected to an Agilent diode array detector. The column used was a Waters XBridge column (50 mm×2.1 mm, 3.5 μm particle size,) and the compounds were eluted with a gradient of 5 to 95% acetonitrile/water+0.1% Ammonia.

Unless otherwise stated herein reactions have not been optimised. Solvents and reagents were purchased from commercial suppliers and used without further purification. Dry solvents were purchased in sure sealed bottles stored over molecular sieves.

The preparations and compounds have been named using the ChemDraw Ultra 12.0 naming application.

PREPARATION 1

4-[(4-Bromophenyl)methyl]morpholine

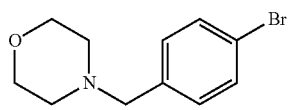 [SMILES: Brc1ccc(CN2CCOCC2)cc1]

To a stirred suspension of morpholine (8.37 g, 96 mmol) and 1-bromo-4-(bromomethyl)benzene (20.00 g, 80 mmol) in acetonitrile and potassium carbonate (27.65 g, 200 mmol) was added at room temperature and the mixture was stirred at 60° C. overnight. After allowing to reach room temperature, the suspension was filtered and the filtrate was absorbed on silica gel. The crude filtrate was purified by column chromatography using a 120 g silica gel cartridge. Solvent A: Hexane. Solvent B: Ethyl Acetate (EtOAc). Gradient: 2 min hold 100% A followed by a 27 min ramp to 40% B and then 3 min hold 40% B. The desired fractions were pooled together and concentrated under reduced pressure to obtain 1 as a white solid (19.5 g, 76 mmol, Yield 89%).

$^1$H NMR (500 MHz; CDCl3) δ 2.43-2.45 (m, 4H), 3.46 (s, 2H), 3.71-3.73 (m, 4H), 7.22-7.24 (m, 2H), 7.44-7.47 (m, 2H) ppm.

Purity by LCMS (UV Chromatogram, 190-450 nm) 94%, rt=5.0 min, m/z 256 (M+H)$^+$

PREPARATION 2

4-[[4-(4,4,5,5-Tetramethyl-1,3,2-dioxaborolan-2-yl)phenyl]methyl]morpholine

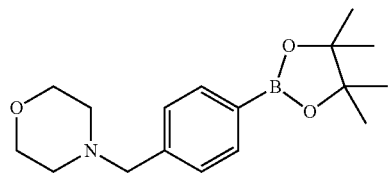 [SMILES: CC1(C)OB(c2ccc(CN3CCOCC3)cc2)OC1(C)C]

To a stirred suspension of 4-[(4-bromophenyl)methyl]morpholine, preparation 1, (5.00 g, mmol), 4,4,5,5-tetramethyl-2-(4,4,5,5-tetramethyl-1,3,2-dioxaborolan-2-yl)-1,3,2-dioxaborolane (5.95 g, 23 mmol) and potassium acetate (4.21 g, 43 mmol) in 1,4-dioxane (60 ml) under argon, Pd(dppf)Cl$_2$ (0.43 g, 0.6 mmol) was added at room temperature. The reaction mixture was heated at 120° C. for 16 h and then filtered through Celite™. Solvents were removed under reduced pressure to obtain a black residue that was taken up in DCM (250 ml) and washed twice with water (2×100 ml).

The organic phase was dried over MgSO$_4$ and solvents were removed under reduced pressure to obtain a black solid. The reaction crude was absorbed on silica gel and purified by column chromatography using a 40 g silica gel cartridge. Solvent A: Hexane. Solvent B: EtOAc. Gradient: 1 min hold 100% A followed by a 14 min ramp to 100% B and then 3 min hold at 40% B. The fractions containing the desired product were pooled together and solvents removed under reduced pressure to obtain the desired compound as a white solid (3.06 g, 10 mmol, Yield 51%).

$^1$H NMR (500 MHz; CDCl$_3$) δ 1.37 (s, 12H), 2.46 (brs, 4H), 3.54 (s, 2H), 3.71-3.73 (m, 4H), 7.37 (d, 2H, J=8.0 Hz), 7.79 (d, 2H, J=8.0 Hz) ppm.

Purity by LCMS (UV Chromatogram, 190-450 nm) 88%, rt=5.5 min, m/z 304 (M+H)$^+$

PREPARATION 3

6-Fluoro-2-hydroxy-quinoline-4-carboxylic acid

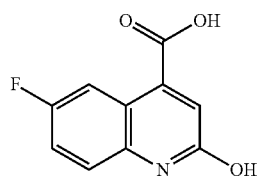 [SMILES: O=C(O)c1cc(O)nc2ccc(F)cc12]

A stirred suspension of 5-fluoroisatin, also known as 5-fluoro-2,3-indoledione, available from Sigma-Aldrich (10.00 g, 61 mmol) and malonic acid (18.91 g, 182 mmol) in acetic acid (400 ml) was refluxed for 16 h. Acetic acid was removed under reduced pressure, the residue was suspended in water (400 ml), filtered and washed with water (300 ml) to give a brown solid. The solid was stirred in NaHCO$_3$ saturated aqueous solution (800 ml) and the insoluble material was filtered off. The filtrate was acidified to pH 1-2 with concen-

PREPARATION 4

2-Chloro-6-fluoro-N-(2-pyrrolidin-1-ylethyl)quinoline-4-carboxamide

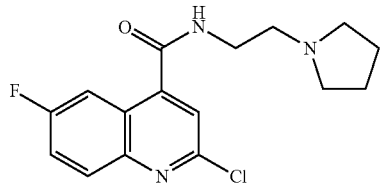 [SMILES: O=C(NCCN1CCCC1)c1cc(Cl)nc2ccc(F)cc12]

To a stirred suspension of 6-fluoro-2-hydroxy-quinoline-4-carboxylic acid (preparation 3) (10.00 g, 48 mmol) in anhydrous DCM (350 ml), was added anhydrous DMF (7 ml) and thionyl chloride (14 ml, 193 mmol) under argon at room temperature. The mixture was refluxed for 3 h and then allowed to cool to room temperature. The solvents were removed under reduced pressure and the residue was dissolved in anhydrous THF (350 ml) under argon. 2-Pyrrolidin-1-ylethanamine, available from Alfa Aesar (18 ml, 145 mmol) was added and the reaction was stirred at room temperature for 16 h. Solvents were removed under vacuum and the residue partitioned between NaHCO$_3$ saturated aqueous solution (250 ml) and DCM (2×200 ml). The organic layers were combined, dried over MgSO$_4$, filtrated and evaporated under reduced pressure. The crude product was purified by column chromatography using a 120 g silica gel cartridge. Solvent A: DCM, Solvent B: 10% MeOH—NH$_3$ in DCM. Gradient: 2 min hold 100% A followed by 18 min ramp to 30% B and then 15 min hold at 30% B. The desired fractions were combined and concentrated to dryness under reduced pressure to obtain the desired compound as an off-white solid (4.59 g, 14 mmol, 27%).

$^1$H NMR (500 MHz; CDCl$_3$) δ 1.83-1.85 (m, 4H), 2.64 (brs, 4H), 2.81 (t, 2H, J=5.5 Hz), 3.65-3.69 (m, 2H), 6.88 (brs, 1H), 7.53 (s, 1H), 7.56 (ddd, 1H, J=2.8 Hz, J=7.9 Hz, J=9.2 Hz), 7.99 (dd, 1H, J=2.8 Hz, J=9.7 Hz), 8.07 (dd, 1H, J=5.4 Hz, J=9.2 Hz) ppm.

$^{19}$F NMR (407.5 MHz; CDCl$_3$) δ−110.03 ppm.

Purity by LCMS (UV Chromatogram, 190-450 nm) 99%, rt=4.8 min, m/z 322 (M+H)$^+$

PREPARATION 5

4-(morpholinomethyl)benzonitrile

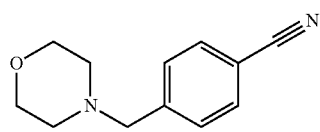 [SMILES: N#Cc1ccc(CN2CCOCC2)cc1]

To a stirred suspension of 4-(bromomethyl)benzonitrile (4.00 g, 20 mmol) in DCM (50 ml), at room temperature, triethylamine (4.12 g, 41 mmol) and morpholine (2.67 g, 31 mmol) were added. The reaction mixture was stirred overnight at room temperature. The solution was then diluted with DCM (100 ml) and washed with NaHCO$_3$ saturated aqueous solution (50 ml), the organic phase was separated, dried over magnesium sulphate and solvents evaporated under reduced pressure. The product was purified by column chromatography using a 80 g silica gel cartridge and the following gradient: Solvent A: DCM, Solvent B: MeOH, 1 min hold at 100% A followed by 12 min ramp to 2.5% B and then 5 min hold at 2.5% B. The desired fractions were combined and concentrated to dryness under reduced pressure to obtain the desired product as a white solid (3 g, 14.8 mmol, Yield 72%).

$^1$H NMR (500 MHz; CDCl3) δ 2.43-2.45 (m, 4H), 3.54 (s, 2H), 3.71 (t, 4H, J=4.7 Hz), 7.46 (d, 2H, J=8.4 Hz), 7.60-7.62 (m, 2H) ppm.

Purity by LCMS (UV Chromatogram, 190-450 nm) 99%, rt=4.4 min, m/z 203 (M+H)$^+$

PREPARATION 6

1-[4-(morpholinomethyl)phenyl]ethanone

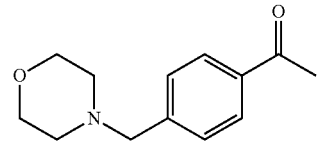 [SMILES: CC(=O)c1ccc(CN2CCOCC2)cc1]

To a stirred suspension of 4-(morpholinomethyl)benzonitrile (preparation 5) (1.00 g, 5 mmol) in toluene (19 ml), 3M methyl magnesium bromide in ethyl ether (5 ml, 15 mmol) was added at room temperature under argon. The resulting suspension was refluxed for 4 h, allowed to reach room temperature and then cooled down to 0° C., acidified with 10% HCl and then heated to reflux for 1 h. The two phases were separated and the aqueous phase rinsed with ethyl acetate, then brought to pH 10 with NH$_4$OH and extracted with DCM. The phases were separated and the organic phase was dried over MgSO$_4$ and concentrated under reduced pressure. The crude product was purified by flash column chromatography using an 80 g silica gel cartridge and eluting with DCM (Solvent A) and MeOH (Solvent B) and the following gradient: 1 min hold 100% A followed by a 12 min ramp to 2.5% B and then 5 min hold at 2.5% B. The desired fractions were concentrated to dryness under vacuum to obtain the desired compound as a white solid (0.79 g, 3.6 mmol, Yield: 70%).

¹H NMR (500 MHz; CDCl3) δ 2.46-2.49 (m, 4H), 2.62 (s, 3H), 3.57 (s, 2H), 3.73 (t, 4H, J=4.7 Hz), 7.45 (d, 2H, J=8.4 Hz), 7.92-7.95 (m, 2H).

Purity by LCMS (UV Chromatogram, 190-450 nm) 96%, rt=4.4 min, m/z 220 (M+H)⁺

PREPARATION 7

6-fluoro-2-[4-(morpholinomethyl)phenyl]quinoline-4-carboxylic acid (VIA)

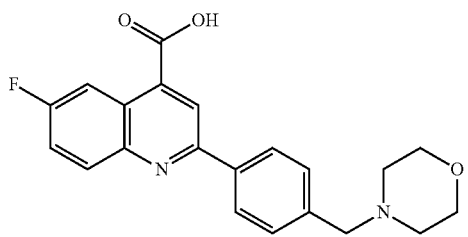 [SMILES: O=C(O)c1cc(-c2ccc(CN3CCOCC3)cc2)nc2ccc(F)cc12]

In a 20 ml microwave vial, 5-fluoroisatin (650 mg, 4 mmol) was suspended in ethanol (7 ml), then, 1-[4-(morpholinomethyl)phenyl]ethanone (preparation 6) (863 mg, 4 mmol) was added followed by water (7 ml). To this suspension potassium hydroxide (2.21 g, 39 mmol) was added at room temperature. The microwave vial was sealed and the reaction mixture was heated at 125° C. for 20 min under microwave irradiation. The resulting solution was diluted with water (50 ml) and adjusted to pH 7-8 with 10% HCl. The resulting precipitate was filtered and washed with water (50 ml) and ethyl acetate (100 ml) to obtain the desired product as an off-white solid (1.1 g, Yield: 76%).

¹H NMR (500 MHz; CDCl3) δ 2.53 (brs, 4H), 3.64 (t, 4H, J=4.4 Hz), 3.68 (s, 2H), 7.54 (d, 2H, J=8.2 Hz), 7.74-7.78 (m, 1H), 8.20 (dd, 1H, J=5.8 Hz, J=9.2 Hz), 8.24 (d, 2H, J=8.2 Hz), 8.47-8.50 (m, 2H) ppm.

Purity by LCMS (UV Chromatogram, 190-450 nm) 99% by UV, rt=3.7 min, m/z 367 (M+H)⁺

PREPARATION 8

6-chloro-2-hydroxy-quinoline-4-carboxylic acid

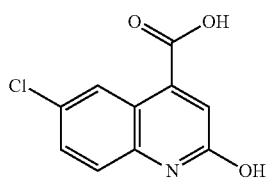 [SMILES: O=C(O)c1cc(O)nc2ccc(Cl)cc12]

A stirred suspension of 6-chloroisatin, also called 6-chloro-1H-indole-2,3-dione, available from Sigma-Aldrich, (10.00 g, 55 mmol) and malonic acid (17.00 g, 165 mmol) in acetic acid (400 ml) was refluxed for 16 h. Acetic acid was removed under reduced pressure, the residue was suspended in water (400 ml), filtered and washed with water (300 ml) to give a grey solid. The solid was stirred in NaHCO₃ saturated aqueous solution (800 ml) and the insoluble material was filtered off. The filtrate was acidified to pH 1-2 with concentrated HCl and the precipitate was filtered, washed with water and dried. The resulting pale yellow solid (9.5 g, 42 mmol, Yield 54%) was used for directly in the synthesis of preparation 9 without further purification. The mixture was analysed by 1H NMR and LCMS: ¹H NMR (500 MHz; d6-DMSO) δ 7.00 (s, 1H), 7.42 (d, 1H, J=8.8 Hz), 7.58 (d, 0.3 H, J=8.9 Hz)*, 7.60-7.62 (m, 1.3 H), 7.81 (dd, 0.3H, J=2.3 Hz, J=8.9 Hz)*, 8.29 (d, 1H, J=2.4 Hz), 12.28 (brs, 1H), 13.22 (brs, 0.3 H)* ppm.

* corresponds to impurity

Purity by LCMS (UV Chromatogram, 190-450 nm) 65%, rt=3.9 min, m/z 224 (M+H)⁺

PREPARATION 9

2,6-dichloro-N-(2-pyrrolidin-1-ylethyl)quinoline-4-carboxamide

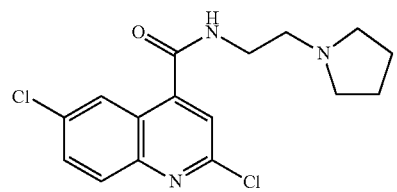 [SMILES: O=C(NCCN1CCCC1)c1cc(Cl)nc2ccc(Cl)cc12]

To a stirred suspension of 6-chloro-2-hydroxy-quinoline-4-carboxylic acid (preparation 8) (8.50 g, 38 mmol) in anhydrous DCM (250 ml), was added anhydrous DMF (2 ml) and thionyl chloride (11 ml, 152 mmol) at room temperature under argon. The mixture was refluxed for 3 h and then allowed to cool to room temperature. The solvents were removed under reduced pressure and the residue was dissolved in anhydrous THF (300 ml) under argon. 2-Pyrrolidin-1-ylethanamine (14 ml, 114 mmol) was added and the reaction was stirred at room temperature for 16 h. Solvents were removed under vacuum and the residue partitioned between NaHCO₃ saturated aqueous solution (250 ml) and DCM (2×250 ml). The organic layers were combined, dried over MgSO₄, filtrated and evaporated under reduced pressure. The crude was purified by column chromatography using a 120 g silica gel cartridge. Solvent A: DCM, Solvent B: 10% MeOH—NH₃ in DCM. Gradient: 2 min hold 100% A followed by 18 min ramp to 30% B and then 15 min hold at 30% B. The relevant fractions were combined and concentrated to dryness under reduced pressure to obtain the desired product as an off-white solid (5.6 g, 16.6 mmol, 43%).

¹H NMR (500 MHz; CDCl₃) δ 1.78-1.81 (m, 4H), 2.57-2.60 (m, 4H), 2.74-2.77 (m, 2H), 3.64 (dt, 2H, J=5.2 Hz, J=11.6 Hz), 6.83 (brs, 1H), 7.48 (s, 1H), 7.70 (dd, 1H, J=2.3 Hz, J=9.0 Hz), 7.97 (d, 1H, J=9.0 Hz), 8.27 (d, 1H, J=2.3 Hz) ppm.

Purity by LCMS (UV Chromatogram, 190-450 nm) 99%, rt=5.1 min, m/z 338 (M+H)+

PREPARATION 10

2-hydroxyquinoline-4-carboxylic acid

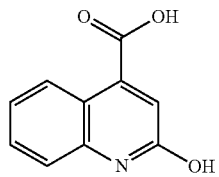 [SMILES: O=C(O)c1cc(O)nc2ccccc12]

A stirred suspension of isatin, also called 1H-indole-2,3-dione, available from Sigma-Aldrich, (3.80 g, 25 mmol) and malonic acid (8.06 g, 77 mmol) in acetic acid (150 ml) was refluxed for 16 h. Acetic acid was removed under reduced pressure, the residue was suspended in water (150 ml), filtered and washed with water (100 ml) to give a brown solid. The solid was stirred in NaHCO$_3$ saturated aqueous solution (200 ml) and the insoluble material was filtered off. The filtrate was acidified to pH 1-2 with concentrated HCl and the precipitate was filtered, washed with water and dried to obtain the desired product as a grey solid (2.2 g, 11.6 mmol, Yield 40%).

$^1$H NMR (500 MHz; d6-DMSO) δ 6.87 (s, 1H), 7.23 (ddd, 1H, J=1.2 Hz, J=7.2 Hz, J=8.3 Hz), 7.41 (dd, 1H, J=0.7 Hz, J=8.3 Hz), 7.55 (ddd, 1H, J=1.4 Hz, J=7.2 Hz, J=8.4 Hz), 8.15 (dd, 1H, J=1.2 Hz, J=8.3 Hz), 12.13 (brs, 1H) ppm.

Purity by LCMS (UV Chromatogram, 190-450 nm) 90%, rt=2.96 min, m/z 190 (M+H)+

PREPARATION 11

2-chloro-N-(2-pyrrolidin-1-ylethyl)quinoline-4-carboxamide

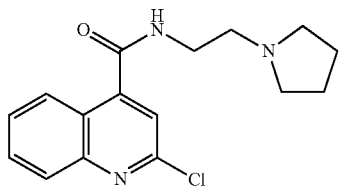 [SMILES: O=C(NCCN1CCCC1)c1cc(Cl)nc2ccccc12]

To a stirred suspension of 2-hydroxyquinoline-4-carboxylic acid (preparation 10) (2.20 g, 12 mmol) in anhydrous DCM (60 ml), was added anhydrous DMF (36 drops) and thionyl chloride (3.3 ml, 46 mmol) under argon at room temperature. The mixture was refluxed for 3 h and then allowed to cool to room temperature. The solvents were removed under reduced pressure and the residue was dissolved in anhydrous THF (37 ml) under argon. 2-Pyrrolidin-1-ylethanamine (4.4 ml, 35 mmol) was added and the reaction was stirred at room temperature for 16 h. Solvents were removed under vacuum and the residue partitioned between NaHCO$_3$ saturated aqueous solution (100 ml) and DCM (2×100 ml). The organic layers were combined, dried over MgSO$_4$, filtrated and evaporated under reduced pressure. The crude was purified by column chromatography using a 24 g silica gel cartridge. Solvent A: DCM, Solvent B: 10% MeOH—NH$_3$ in DCM. Gradient: 2 min hold 100% A followed by 18 min ramp to 40% B and then hold 5 min at 40% B. The desired fractions were combined and concentrated to dryness under reduced pressure to obtain the desired material as a white solid (2 g, 6.6 mmol, 56%).

$^1$H NMR (500 MHz; CDCl$_3$) δ 1.76-1.19 (m, 4H), 2.54-2.57 (m, 4H), 2.73-2.75 (m, 2H), 3.64 (dt, 2H, J=5.2 Hz, J=11.7 Hz), 6.78 (brs, 1H), 7.45 (s, 1H), 7.60 (ddd, 1H, J=1.2 Hz, J=6.9 Hz, J=8.3 Hz), 7.76 (ddd, 1H, J=1.4 Hz, J=6.9 Hz, J=8.4 Hz), 8.03 (d, 1H, J=8.5 Hz), 8.22 (d, 1H, J=8.4 Hz) ppm.

Purity by LCMS (UV Chromatogram, 190-450 nm) 99%, rt=4.5 min, m/z 304 (M+H)+

PREPARATION 12

4-(4-bromo-3-fluorobenzyl)morpholine

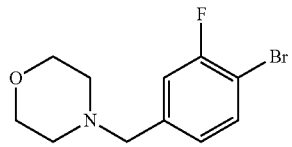 [SMILES: Fc1cc(CN2CCOCC2)ccc1Br]

A mixture of morpholine (0.215 ml, 2.46 mmol) and 4-bromo-3-fluorobenzaldehyde, available from Alfa Aesar, (500 mg, 2.46 mmol) was prepared in chloroform (8 ml) at room temperature and heated to 58-60° C. in a sealed tube for 1 h. The mixture was then cooled to room temperature and sodium triacetoxyborohydride (783 mg, 3.69 mmol) was added and the mixture heated again to 58-60° C. in a sealed tube for 12 h. The mixture was then allowed to cool to room temperature, diluted with water (4 ml), shaken vigorously and the mixture filtered through a phase separator and the filtrate concentrated in vacuo. The mixture was then purified by SCX-2 chromatography (Eluent: dichloromethane (2×10 ml), 10% methanol/dichloromethane (2×10 ml), methanol (2×10 ml), 7M NH3 in methanol/dichloromethane (2×10 ml) to afford 4-(4-bromo-3-fluorobenzyl)morpholine as a colourless oil (447 mg, 1.63 mmol, 66%).

$^1$H NMR (500 MHz; CDCl$_3$) δ 2.46 (brs, 4H), 3.47 (brs, 2H), 3.73 (brs, 4H), 7.03 (brs, 1H), 7.17 (brd, 1H, J=6.8 Hz), 7.48 (t, 1H, J=7.7 Hz) ppm. Purity by LCMS (UV Chromatogram, 190-450 nm) 95%, rt=5.2 min, m/z 274 (M+H)+

PREPARATION 13

4-(4-bromo-2,6-difluorobenzyl)morpholine

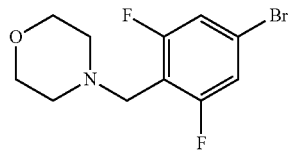

A mixture of 4-bromo-2,6-difluorobenzaldehyde, available from Sigma-Aldrich, (500 mg, 2.26 mmol) and morpholine (0.198 ml, 2.26 mmol) was prepared in chloroform (10 ml) at room temperature and heated to 58-60° C. in a sealed tube for 1 h. The mixture was then cooled to room temperature and sodium triacetoxyborohydride (719 mg, 3.39 mmol)

was added and the mixture heated again to 58-60° C. in a sealed tube for 60 h. The mixture was allowed to cool down to room temperature and then washed with water (5 ml), filtered through a phase separator and concentrated in vacuo. Crude ¹HNMR (CDCl₃) suggested an 8:2 mixture of the desired amine to the imine product. After initial chromatography (1-5% methanol/dichloromethane) which did not separate products, mixture was purified by preparative HPLC to afford 4-(4-bromo-2,6-difluorobenzyl)morpholine as a colourless oil (247 mg, 0.85 mmol, 37%).

¹H NMR (500 MHz; CDCl₃) δ 2.48 (t, 4H, J=4.4 Hz), 3.62 (t, 2H, J=1.6 Hz), 3.68 (t, 4H, J=4.7 Hz), 7.09 (d, 2H, J=6.8 Hz) ppm.

Purity by LCMS (UV Chromatogram, 190-450 nm) 95%, rt=4.2 min, m/z 292 (M+H)⁺

PREPARATION 14

4-(4-bromobenzyl)thiomorpholine 1,1-dioxide

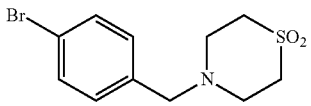 [SMILES: O=S1(=O)CCN(Cc2ccc(Br)cc2)CC1]

A mixture of thiomorpholine 1,1-dioxide (270 mg, 2.0 mmol) in DMF (10 ml) was prepared at room temperature and sodium hydride (60 wt % in oil, 96 mg, 2.40 mmol) added in one portion and the mixture stirred at room temperature for 1 h. 1-Bromo-4-(bromomethyl)benzene was then added in one portion and the mixture stirred overnight for 17.5 h under argon. The mixture was then quenched with saturated aqueous ammonium chloride solution (10 ml) and diluted with ethyl acetate (30 ml). The mixture was partitioned and the aqueous layer removed. The organic layers were then washed with 5% aqueous lithium chloride solution (2×10 ml), brine (10 ml), dried over magnesium sulphate and the solvent removed under reduced pressure. The crude product was then purified by column (0-5% methanol/dichloromethane) to afford 4-(4-bromobenzyl)thiomorpholine 1,1-dioxide as a colourless solid (283 mg, 0.93 mmol, 47%).

¹H NMR (500 MHz; CDCl₃) δ 2.98 (brs, 4H), 3.06 (brs, 4H), 3.60 (s, 2H), 7.20 (d, 2H, J=8.1 Hz), 7.47 (d, 2H, J=8.3 Hz) ppm.

Purity by LCMS (UV Chromatogram, 190-450 nm) 95%, rt=5.0 min, m/z 306 (M+H)⁺

PREPARATION 15

1-(2-chloro-4-methylphenyl)ethanone

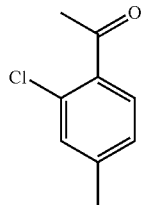

A mixture of 2-chloro-4methylbenzonitrile (2.00 g, 13.19 mmol) in toluene (25 ml), was prepared at room temperature and 3M bromo methyl magnesium (13.2 ml, 39.68 mmol) in diethylether, 3M was added dropwise and the mixture then heated to reflux (100-110° C.) for 16 h. The mixture was then cooled to 0° C. and then adjusted to pH 2 with 2M aqueous HCl. The mixture was then heated to reflux as above for 2 h. The mixture was then basified with 2M NaOH to pH 11, extracted with EtOAc (100 ml), the organic phase dried over MgSO₄ and then concentrated under reduced pressure. The crude product was then purified by column chromatography (0-10% EtOAc/Hexanes) to afford 1-(2-chloro-4-methylphenyl)ethanone as a pale yellow oil (1.60 g, 9.50 mmol, 72%).

¹H NMR (500 MHz; CDCl₃) δ 2.37 (s, 3H), 2.64 (s, 3H), 7.12 (d, 1H, J=8.0 Hz), 7.24 (s, 1H), 7.51 (d, 1H, J=7.9 Hz) ppm.

PREPARATION 16

1-(4-(bromomethyl)-2-chlorophenyl)ethanone

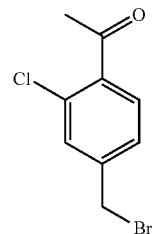

A mixture of 1-(2-chloro-4-methylphenyl)ethanone (1.6 g, 9.50 mmol) (preparation 15) and chlorobenzene (60 ml) was prepared at room temperature and N-bromosuccinimide (NBS) (1.86 g, 10.44 mmol) added followed by a catalytic amount of benzoyl peroxide (ca. 1.5 mg, 0.005 mmol), and the resulting mixture was heated to 140-145° C. for 16 h. The mixture was then allowed to cool to room temperature, diluted with toluene (50 ml) and filtered through a celite pad. The pad was washed with toluene (2×50 ml) and the filtrate concentrated under reduced pressure and purified by column chromatography (0-10% EtOAc/Hexanes) to afford 1-(4-(bromomethyl)-2-chlorophenyl)ethanone (1.65 g, 6.65 mmol, 70%) as a yellow oil.

¹H NMR (500 MHz; CDCl₃) δ 2.65 (s, 3H), 4.43 (s, 2H), 7.34 (dd, 1H, J=1.3, 8.0 Hz), 7.46 (s, 1H), 7.54 (d, 1H, J=7.9 Hz) ppm.

PREPARATION 17

1-(2-chloro-4-(morpholinomethyl)phenyl)ethanone

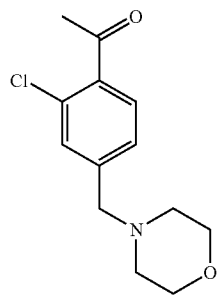 [SMILES: CC(=O)c1ccc(CN2CCOCC2)cc1Cl]

A mixture of 1-(4-(bromomethyl)-2-chlorophenyl)ethanone (1.65 g, 6.65 mmol) (preparation 16) and acetonitrile (25 ml) was prepared at room temperature and stirred under nitrogen. Potassium carbonate (1.10 g 7.98 mmol) was then added followed by morpholine (0.695 ml, 7.98 mmol) and the mixture stirred at room temperature. After 2 h, TLC indicated the presence of both product and starting material. The mixture was then heated under nitrogen to 40° C. for 16 h, then allowed to cool to room temperature, filtered to remove excess carbonate and filtrate concentrated under reduced pressure. The mixture was then diluted in DCM (30 ml), washed with water (2×10 ml), filtered through a phase separator and the filtrate concentrated under reduced pressure. The crude mixture was purified by column chromatography (40-100% EtOAc/hexane) to afford 1-(2-chloro-4-(morpholinomethyl)phenyl)ethanone as a yellow oil (1.08 g, 4.25 mmol, 64%).

$^1$H NMR (500 MHz; CDCl$_3$) δ 2.44 (brs, 4H), 2.65 (s, 3H), 3.49 (s, 2H), 3.72 (t, 4H, J=4.6 Hz), 7.29 (dd, 1H, J=1.5, 7.9 Hz), 7.43 (brs, 1H), 7.55 (d, 1H, J=7.9 Hz) ppm.

Purity by LCMS (UV Chromatogram, 190-450 nm) 95%, rt=4.8 min, m/z 254 (M+H)$^+$

PREPARATION 18

2-(2-chloro-4-(morpholinomethyl)phenyl)-6-fluoroquinoline-4-carboxylic acid

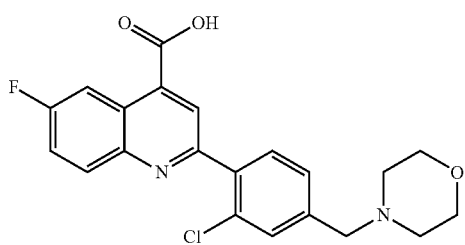 [SMILES: O=C(O)c1cc(-c2ccc(CN3CCOCC3)cc2Cl)nc2ccc(F)cc12]

A mixture of 5-fluoroisatin (702 mg, 4.25 mmol) and 1-(2-chloro-4-(morpholinomethyl)phenyl)ethanone (1.08 g, 4.25 mmol) (preparation 17) was prepared in EtOH/water (1:1) (10 ml) and then KOH (2.38 g, 42.49 mmol) was added and the resulting mixture heated under microwave irradiation at mw, 125° C. for 20 mins. The mixture was then diluted with water (10 ml) acidified to pH3 with 2M aqueous HCl, stirred for 16 h at room temperature and the resulting precipitate filtered, washed with water (2×10 ml) and concentrated under reduced pressure to afford 2-(2-chloro-4-(morpholinomethyl)phenyl)-6-fluoroquinoline-4-carboxylic acid as an orange solid (503 mg, 1.25 mmol, 30%).

$^1$H NMR (500 MHz; d6-DMSO) δ 2.54 (brs, 4H), 3.64 (s, 4H), 3.70 (brs, 2H), 7.50 (d, 1H, J=8.1 Hz), 7.62 (s, 1H), 7.73 (brd, 1H, J=7.9 Hz), 7.84 (dt, 1H, J=2.9, 8.2 Hz), 8.24 (dd, 1H, J=5.8, 9.2 Hz), 8.29 (s, 1H), 8.56 (dd, 1H, J=2.9, 11.0 Hz) ppm.

LCMS (UV Chromatogram, 190-450 nm) 95%, rt=1.3 min, m/z 399 (M−H)$^−$

EXAMPLE 1

6-Fluoro-2-[4-(morpholinomethyl)phenyl]-N-(2-pyrrolidin-1-ylethyl)quinoline-4-carboxamide, Example compound 1 in Scheme 2

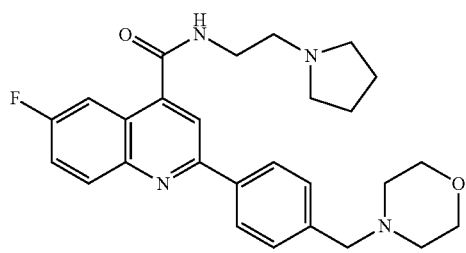 [SMILES: O=C(NCCN1CCCC1)c1cc(-c2ccc(CN3CCOCC3)cc2)nc2ccc(F)cc12]

In a sealed microwave tube, a suspension of 2-chloro-6-fluoro-N-(2-pyrrolidin-1-ylethyl)quinoline-4-carboxamide (preparation 4) (2.00 g, 6 mmol), [4-(morpholinomethyl)phenyl]boronic acid, hydrochloride, available from UORSY, (3.20 g, 12 mmol), potassium phosphate (2.63 g, 12 mmol) and tetrakis(triphenylphosphine)palladium (0) (0.21 g, 0.19 mmol) in DMF/Water 3/1 (40 ml) was heated at 130° C. under microwave irradiation for 30 min. The reaction was filtered through Celite™ and solvents were removed under reduced pressure. The resulting residue was taken up in DCM (150 ml) and washed twice with NaHCO$_3$ saturated aqueous solution (2×100 ml). The organic layer was separated, dried over MgSO$_4$ and concentrate to dryness under reduced pressure. The reaction crude was purified by flash column chromatography using an 80 g silica gel cartridge and eluting with DCM (Solvent A) and MeOH (Solvent B) and the following gradient: 1 min hold 100% A, followed by a 30 min ramp to 10% B, and then 15 min hold at 10% B. The fractions containing product were pooled together and concentrated to dryness under vacuum to obtain the desired product as an off-white solid (1 g). The product was dissolved in methanol (100 ml) and 3-mercaptopropyl ethyl sulfide Silica (Phosphonics, SPM-32, 60-200 uM) was added. The suspension was stirred at room temperature over for 2 days and then at 50° C. for 1 h. After cooling to room temperature, the scavenger was filtered off and washed with methanol (30 ml). The solvent was removed under reduced pressure and the product was further purified by preparative HPLC. The fractions containing product were pooled together and freeze dried to obtain the desired product as a white solid (0.6 g, 1.3 mmol, Yield 20%).

$^1$H NMR (500 MHz; CDCl$_3$) δ 1.81-1.84 (m, 4H), 2.50-2.52 (m, 4H), 2.63 (brs, 4H), 2.82 (t, 2H, J=5.9 Hz), 3.61 (s, 2H), 3.71 (dd, 2H, J=5.4 Hz, J=11.4 Hz), 3.74-3.76 (m, 4H), 6.84 (brs, 1H), 7.52-7.57 (m, 3H), 7.97-8.00 (m, 2H), 8.13 (d, 2H, J=8.2 Hz), 8.21 (dd, 1H, J=5.5 Hz, J=9.2 Hz) ppm. $^{19}$F NMR (407.5 MHz; CDCl$_3$) δ−111.47 ppm.

Purity by LCMS (UV Chromatogram, 190-450 nm) 99%, rt=5.7 min, m/z 463 (M+H)+ HRMS (ES+) found 463.2501 [M+H]+, C27H32F1N4O2 requires 463.2504.

EXAMPLE 2

6-Fluoro-2-[4-(morpholinomethyl)phenyl]-N-(2-pyrrolidin-1-ylethyl)quinoline-4-carboxamide; fumaric acid salt, compound (IB) in Scheme 2

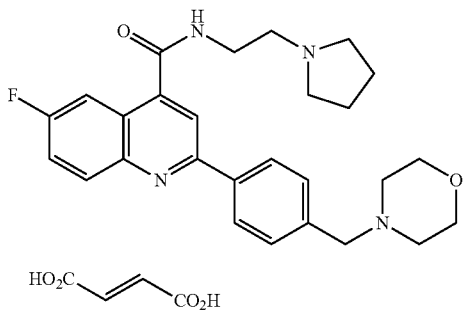 [SMILES: O=C(NCCN1CCCC1)c1cc(-c2ccc(CN3CCOCC3)cc2)nc2ccc(F)cc12 ; O=C(O)/C=C/C(=O)O]

The starting free base (example 1) (0.58 g, 1 mmol) was dissolved in dry ethanol (10 ml) and added dropwise to a stirred solution of fumaric acid (0.15 g, 1 mmol) in dry ethanol (9 ml). The mixture was stirred at room temperature for 1 h. The white precipitate was filtered, washed with ethanol (20 ml) and then dissolved in 10 ml of water and freeze dried to obtain the desired salt as a white solid (0.601 g, 1 mmol, Yield 82%).

$^1$H NMR (500 MHz; d6-DMSO) δ 1.83-1.86 (m, 4H), 2.41 (brs, 4H), 2.94 (brs, 4H), 3.03 (t, 2H, J=6.2 Hz), 3.57 (s, 2H), 3.60-3.65 (m, 6H), 6.47 (s, 2H), 7.51 (d, 2H, J=8.25), 7.74-7.78 (m, 1H), 8.06 (dd, 1H, J=2.9 Hz, J=10.4 Hz), 8.17 (dd, 1H, J=5.7 Hz, J=9.3 Hz), 8.24-8.26 (m, 3H), 9.24 (t, 1H, J=5.5 Hz) ppm. $^{19}$F NMR (407.5 MHz; d6-DMSO) δ-112.30 ppm.

Purity by LCMS (UV Chromatogram, 190-450 nm) 99%, rt=5.3 min, m/z 463 (M+H)+

EXAMPLE 1A

Alternative synthesis of 6-fluoro-2-[4-(morpholinomethyl)phenyl]-N-(2-pyrrolidin-1-ylethyl)quinoline-4-carboxamide, Example compound 1A in Scheme 4

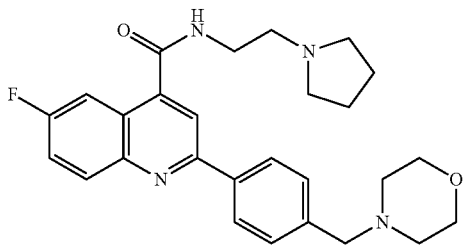 [SMILES: O=C(NCCN1CCCC1)c1cc(-c2ccc(CN3CCOCC3)cc2)nc2ccc(F)cc12]

To a stirred suspension of 6-fluoro-2-[4-(morpholinomethyl)phenyl]quinoline-4-carboxylic acid (preparation 7) (2.20 g, 6 mmol) in DCM (100 ml) at room temperature, 2-chloro-4,6-dimethoxy-1,3,5-triazine (CDMT) (1.26 g, 7 mmol) and 4-methylmorpholine (NMO) (1.33 ml, 12 mmol) were added. The reaction mixture was stirred at room temperature for 1 h and then 2-pyrrolidin-1-ylethanamine (0.77 ml, 6 mmol) was added and stirred at room temperature for further 3 h. The reaction mixture was washed with NaHCO$_3$ saturated aqueous solution (2×100 ml) and the organic phase was separated, dried over MgSO$_4$ and concentrated under reduced pressure. The resulting residue was absorbed on silica gel and purified by flash column chromatography using an 80 g silica gel cartridge and eluting with DCM (Solvent A) and MeOH (Solvent B) and the following gradient: 2 min hold 100% A followed by a 30 min ramp to 10% B and then 15 min hold at 10% B. The desired fractions were concentrated to dryness under vacuum to obtain the crude product as a yellow solid (95% purity by LCMS). The sample was further purified by a second column chromatography using a 40 g silica gel cartridge, eluting with DCM (Solvent A) and 10% NH$_3$-MeOH in DCM (Solvent B) and the following gradient: 2 min hold 100% A, followed by a 10 min ramp to 23% B and then 15 min hold at 23% B. The desired fractions were concentrated to dryness under vacuum to obtain product as a white solid (1 g). Re-crystallisation form acetonitrile (18 ml) yielded the title compound as a white solid (625 mg, 1.24 mmol, 20%).

$^1$H NMR (500 MHz; CDCl$_3$) δ 1.81-1.84 (m, 4H), 2.50-2.52 (m, 4H), 2.63 (brs, 4H), 2.82 (t, 2H, J=5.9 Hz), 3.61 (s, 2H), 3.71 (dd, 2H, J=5.4 Hz, J=11.4 Hz), 3.74-3.76 (m, 4H), 6.84 (brs, 1H), 7.52-7.57 (m, 3H), 7.97-8.00 (m, 2H), 8.13 (d, 2H, J=8.2 Hz), 8.21 (dd, 1H, J=5.5 Hz, J=9.2 Hz) ppm.

$^1$H NMR (500 MHz; d6-DMSO) δ 1.72-1.75 (m, 4H), 2.41 (brs, 4H), 2.56 (brs, 4H), 2.67 (t, 2H, J=6.6 Hz), 3.49-3.52 (m, 2H), 3.56 (s, 2H), 3.60-3.61 (m, 4H), 7.52 (d, 2H, J=8.3 Hz), 7.73-7.77 (m, 1H), 8.07 (dd, 1H, J=2.9 Hz, J=10.4 Hz), 8.18-8.21 (m, 2H), 8.26 (d, 2H, J=8.3 Hz), 8.85 (t, 1H, J=6.6 Hz) ppm.

$^{13}$C NMR (125 MHz; d$^6$-DMSO$_3$) δ 23.2, 38.4, 53.2, 53.5, 54.5, 62.1, 66.2, 109.0, 109.1, 117.3, 120.1, 120.3, 124.1, 124.2, 127.1, 129.4, 132.2, 132.3, 136.8, 139.9, 142.8, 145.2, 155.3, 159.0, 161.0, 166.1 ppm.

$^{19}$F NMR (500 MHz; d$^6$-DMSO) δ-112.47 ppm.

Purity by LCMS (UV Chromatogram, 190-450 nm) 99%, rt=5.0 min, m/z 463 (M+H)+

EXAMPLE 3

6-chloro-2-[4-(morpholinomethyl)phenyl]-N-(2-pyrrolidin-1-ylethyl)quinoline-4-carboxamide

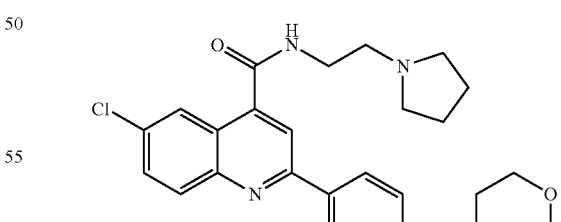

In a sealed 5 ml microwave vial, a suspension of 2,6-dichloro-N-(2-pyrrolidin-1-ylethyl)quinoline-4-carboxamide (preparation 9) (158 mg, 0.47 mmol), [4-(morpholinomethyl)phenyl]boronic acid hydrochloride (240 mg, 0.93 mmol), potassium phosphate (198 mg, 0.93 mmol) and tetrakis(triphenylphosphine)palladium (0) (16 mg, 0.01 mmol) in DMF/Water 3/1 (4 ml) was heated at 130° C. under microwave irradiation for 30 minutes. The reaction was filtered through Celite™ and solvents were removed under reduced pressure. The resulting residue was taken up in DCM (50 ml) and washed with NaHCO$_3$ saturated aqueous solution (25 ml). The organic layer was separated and dried over MgSO4 before concentration to dryness under reduced pressured. The reaction crude was purified by flash column chromatography using a 12 g silica gel cartridge and eluting with DCM (Solvent A) and MeOH (Solvent B) and the following gradient: 2 min hold 100% A followed by a 18 min ramp to 10% B and then 5 min hold at 10% B. The desired fractions were pooled together and concentrated to dryness under vacuum to obtain the crude material as an off-white solid (100 mg). The product was further purified by mass directed autopreparative HPLC. The fractions containing product were pooled together and freeze dried to obtain the desired material as a white solid (68 mg, 0.14 mmol, Yield 30%).

$^1$H NMR (500 MHz; CDCl$_3$) δ 1.78-1.81 (m, 4H), 2.48 (brs, 4H), 2.62 (brs, 4H), 2.80 (t, 2H, J=5.9 Hz), 3.58 (s, 2H), 3.69 (dd, 2H, J=5.3 Hz, J=11.5 Hz), 3.72-3.74 (m, 4H), 6.90 (brs, 1H), 7.50 (d, 2H, J=8.3 Hz), 7.68 (dd, 1H, J=2.3 Hz, J=9.0 Hz), 7.96 (s, 1H), 8.10-8.12 (m, 3H), 8.27 (d, 1H, J=2.3 Hz) ppm.

Purity by LCMS (UV Chromatogram, 190-450 nm) 99%, rt=5.4 min, m/z 479 (M+H)$^+$

HRMS (ES+) found 479.2196 [M+1], C27H32ClN4O2 requires 479.2208

EXAMPLE 4

2-[4-(morpholinomethyl)phenyl]-N-(2-pyrrolidin-1-ylethyl)quinoline-4-carboxamide

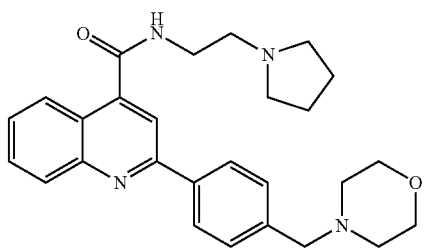 [SMILES: O=C(NCCN1CCCC1)c1cc(-c2ccc(CN3CCOCC3)cc2)nc2ccccc12]

In a sealed 5 ml microwave tubed, a suspension of 2-chloro-N-(2-pyrrolidin-1-ylethyl)quinoline-4-carboxamide (preparation 11) (200 mg, 0.66 mmol), 4-[[4-(4,4,5,5-tetramethyl-1,3,2-dioxaborolan-2-yl)phenyl]methyl]morpholine (preparation 2) (399 mg, 1.31 mmol), potassium phosphate (419 mg, 1.97 mmol) and tetrakis(triphenylphosphine)palladium (0) (22 mg, 0.02 mmol) in DMF/Water 3/1 (4 ml) was heated at 130° C. under microwave irradiation for 30 minutes. The reaction was filtered through Celite™ and solvents were removed under reduced pressure. The resulting residue was taken up in DCM (50 ml) and washed with NaHCO$_3$ saturated aqueous solution (25 ml). The organic layer was separated and dried over MgSO4 before concentration to dryness. The reaction crude was purified by preparative HPLC. The fractions containing product were pooled together and freeze dried to obtain the desired compound as a white solid (220 mg, 0.49 mmol, Yield 57%).

$^1$H NMR (500 MHz; CDCl$_3$) δ 1.76-1.78 (m, 4H), 2.48 (brs, 4H), 2.57 (brs, 4H), 2.77 (t, 2H, J=6.0 Hz), 3.58 (s, 2H), 3.68 (dd, 2H, J=5.5 Hz, J=11.3 Hz), 3.72-3.74 (m, 4H), 6.78 (brs, 1H), 7.50 (d, 2H, J=8.1 Hz), 7.55-7.58 (m, 1H), 7.74-7.77 (m, 1H), 7.93 (s, 1H), 8.11 (d, 2H, J=8.1 Hz), 8.19 (d, 1H, J=8.3 Hz), 8.23 (d, 1H, J=8.4 Hz) ppm.

Purity by LCMS (UV Chromatogram, 190-450 nm) 99%, rt=4.8 min, m/z 445 (M+H)$^+$ HRMS (ES+) found 445.2599 [M+1], C27H33N4O2 requires 445.2598

EXAMPLE 5

2-[4-(morpholinomethyl)phenyl]-N-(2-pyrrolidin-1-ylethyl)quinoline-4-carboxamide; fumaric acid salt

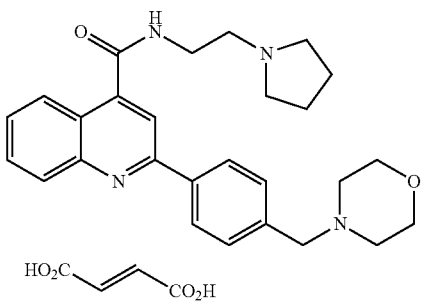 [SMILES: O=C(NCCN1CCCC1)c1cc(-c2ccc(CN3CCOCC3)cc2)nc2ccccc12 ; O=C(O)/C=C/C(=O)O]

The starting free base (Example 4) (95 mg, 0.21 mmol) was dissolved in dry ethanol (1.5 ml) and added dropwise to a solution of fumaric acid (24 mg, 0.21 mmol) in dry ethanol (1.5 ml) at room temperature. The mixture was stirred at room temperature for 1 h. The white precipitate was filtered, washed with ethanol (3 ml) and then dissolved in 10 ml of water and freeze dried to obtain the desired salt as a white solid (80 mg, Yield 67%).

$^1$H NMR (500 MHz; d6-DMSO) δ 1.79-1.80 (m, 4H), 2.40 (brs, 4H), 2.80 (brs, 4H), 2.90 (t, 2H, J=6.6 Hz), 3.56-3.61 (m, 8H), 6.52 (s, 2H), 7.50 (d, 2H, J=8.1), 7.61-7.64 (m, 1H), 7.80-7.83 (m, 1H), 8.10-8.12 (m, 2H), 8.23-8.26 (m, 3H), 9.02 (t, 1H, J=5.5 Hz) ppm.

Purity by LCMS (UV Chromatogram, 190-450 nm) 99%, rt=4.9 min, m/z 445 (M+1).

EXAMPLE 6

6-fluoro-2-(3-fluoro-4-(morpholinomethyl)phenyl)-N-(2-(pyrrolidin-1-yl)ethyl)quinoline-4-carboxamide

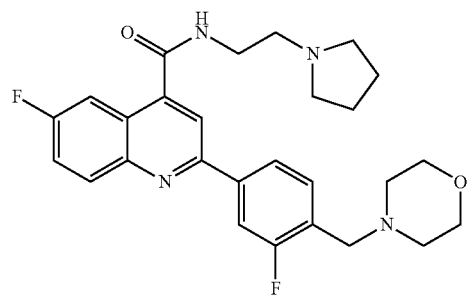 [SMILES: O=C(NCCN1CCCC1)c1cc(-c2ccc(CN3CCOCC3)c(F)c2)nc2ccc(F)cc12]

A mixture of 4-bromo-2-fluorobenzaldehyde (500 mg, 2.46 mmol) and morpholine (0.215 ml, 215 mg, 2.46 mmol) was prepared in chloroform (10 ml) at room temperature and heated to 58-60° C. in a sealed tube for 1 h. The mixture was then cooled to room temperature and sodiumtriacetoxyborohydride (783 mg, 3.69 mmol) was added and the mixture heated again to 58-60° C. in a sealed tube for 16 h. The mixture was then concentrated in vacuo and then diluted with dichloromethane (20 ml), washed with water (2×5 ml), filtered through a phase separator and the filtrate concentrated in vacuo. Crude ¹HNMR in CDCl₃ showed 4-(4-bromo-2-fluorobenzyl)morpholine as the desired product in quantitative yield. 4-(4-Bromo-2-fluorobenzyl)morpholine was then dissolved in 1,4-dioxane (10 ml) and to it added bis(pinacolato)diboron (751 mg, 2.96 mmol), potassium acetate (532 mg, 5.42 mmol) and finally, [1,1'-Bis(diphenylphosphino)ferrocene]dichloropalladium(II) (90 mg, 0.12 mmol) added and the mixture heated under microwave irradiation at 120° C. for 30 min. The mixture was concentrated in vacuo, diluted with dichloromethane (10 ml), washed with water (5 ml) and filtered through a phase separator. The filtrate was concentrated in vacuo to afford the boronic ester intermediate as determined by ¹HNMR in CDCl₃. The crude product was then dissolved in DMF (10 ml) at room temperature and 2-chloro-6-fluoro-N-(2-(pyrrolidin-1-yl)ethyl)quinoline-4-carboxamide (preparation 4) (396 mg, 0.41 mmol), potassium phosphate tribasic (522 mg, 2.46 mmol) in water (2 ml), bis(triphenylphosphine)palladium(II) dichloride (71 mg, 0.062 mmol) were added. The reaction mixture was heated under microwave irradiation for 30 minutes at 120° C. The mixture was then allowed to cool to room temperature, diluted in ethyl acetate (50 ml), washed with 5% lithium chloride aqueous solution (3×20 ml), brine (20 ml) and the mixture concentrated in vacuo and purified by column chromatography (0-10% 7M ammonia in methanol/dichloromethane). The crude product mixture was dissolved in dichloromethane and filtered through a Celite™ pad using dichloromethane/methanol as eluent. The mixture was purified by preparative HPLC to afford the desired material as an off-white solid (102 mg, 0.21 mmol, 9% over 3 steps).

¹H NMR (500 MHz; CDCl₃) δ 1.79 (p, 4H, J=3.1 Hz), 2.53 (t, 4H, J=4.3 Hz), 2.59 (t, 4H, J=6.6 Hz), 2.78 (t, 2H, J=6.0 Hz), 3.65 (s, 2H), 3.69 (q, 2H, J=5.3 Hz), 3.73 (t, 4H, J=4.6 Hz), 6.78 (brs, 1H), 7.52-7.57 (m, 2H), 7.88 (s, 1H), 7.90 (d, 1H, J=1.6 Hz), 7.97-7.95 (m, 2H), 8.19 (dd, 1H, J=5.5 Hz, J=9.3 Hz) ppm.

Purity by LCMS (UV Chromatogram, 190-450 nm) 95%, rt=4.3 min, m/z 481 (M+H)⁺

EXAMPLE 7

6-fluoro-2-(2-fluoro-4-(morpholinomethyl)phenyl)-N-(2-(pyrrolidin-1-yl)ethyl)quinoline-4-carboxamide

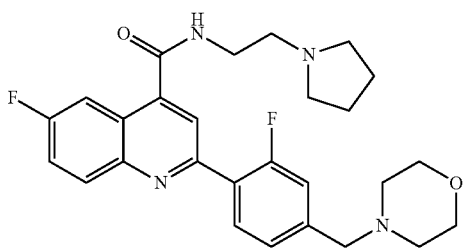 [SMILES: O=C(NCCN1CCCC1)c1cc(-c2ccc(CN3CCOCC3)cc2F)nc2ccc(F)cc12]

To a solution of 4-(4-bromo-3-fluorobenzyl)morpholine (preparation 12) (445 mg, 1.62 mmol) in 1,4-dioxane (4 ml), bis(pinacolato)diboron (495 mg, 1.95 mmol), potassium acetate (350 mg, 3.57 mmol) and [1,1'-Bis(diphenylphosphino)ferrocene]dichloropalladium(II) (59 mg, 0.081 mmol) were added and the mixture was heated under microwave irradiation at 120° C. for 30 minutes. The reaction mixture was concentrated in vacuo, diluted with dichloromethane (10 ml), washed with water (5 ml) and filtered through a phase separator. The filtrate was concentrated in vacuo to afford the boronic ester intermediate as determined by ¹H NMR in CDCl₃. The crude boronic ester was then dissolved in DMF (10 ml) and 2-chloro-6-fluoro-N-(2-(pyrrolidin-1-yl)ethyl)quinoline-4-carboxamide (preparation 4) (261 mg, 0.81 mmol), potassium phosphate tribasic (344 mg, 1.62 mmol) in water (2 ml), bis(triphenylphosphine) palladium(II) dichloride (71 mg, 0.062 mmol) were added. The reaction mixture was heated under microwave irradiation for 30 minutes at 120° C. The reaction crude was filtered through a Celite™ pad and washed with ethyl acetate (4×10 ml). The combined organic phases were washed with 5% lithium chloride aqueous solution (3×10 ml), brine (10 ml), dried over magnesium sulphate and concentrated in vacuo. The mixture was purified by mass directed autoprep HPLC to afford the desired product as an off-white solid (193 mg, 0.40 mmol, 25% yield over 2 steps).

¹H NMR (500 MHz; CDCl3) δ 1.93 (brs, 4H), 2.49 (t, 4H, J=4.4 Hz), 2.59 (brs, 4H), 2.78 (brs, 2H), 3.56 (s, 2H), 3.74 (t, 4H, J=4.7 Hz), 3.78 (brs, 2H), 7.23-7.30 (m, 2H), 7.53 (ddd, 1H, J=2.8 Hz, J=8.1 Hz, J=9.3 Hz), 8.02-8.08 (m, 3H), 8.19 (dd, 1H, J=5.5 Hz, J=9.3 Hz) ppm.

Purity by LCMS (UV Chromatogram, 190-450 nm) 95%, rt=0.68 min, m/z 481 (M+H)⁺

EXAMPLE 8

2-(3,5-difluoro-4-(morpholinomethyl)phenyl)-6-fluoro-N-(2-(pyrrolidin-1-yl)ethyl)quinoline-4-carboxamide

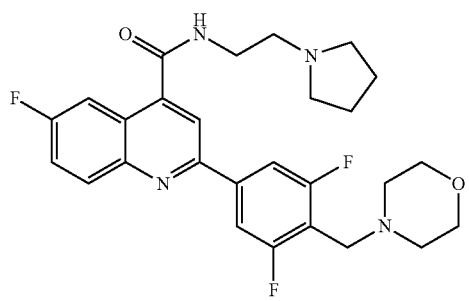 [SMILES: O=C(NCCN1CCCC1)c1cc(-c2cc(F)c(CN3CCOCC3)c(F)c2)nc2ccc(F)cc12]

To a solution of 4-(4-bromo-2,6-difluorobenzylmorpholine (preparation 13) (245 mg, 0.84 mmol) in 1,4-dioxane (4 ml), and bis(pinacolato)diboron (256 mg, 1.01 mmol), potassium acetate (181 mg, 3.57 mmol) and [1,1'-Bis(diphenylphosphino)ferrocene]dichloropalladium(II) (31 mg, 0.042 mmol) were added. The reaction mixture was heated under microwave irradiation at 120° C. for 30 minutes. The reaction mixture was concentrated in vacuo, diluted with dichloromethane (10 ml), washed with water (5 ml) and filtered through a phase separator. The filtrate was concentrated in vacuo to afford the boronic ester intermediate as determined by ¹H NMR in CDCl₃ and LCMS. The crude boronic ester was then dissolved in DMF (10 ml) and 2-chloro-6-fluoro-N-(2-(pyrrolidin-1-yl)ethyl)quinoline-4-carboxamide (preparation 4) (135 mg, 0.42 mmol), potassium phosphate tribasic (178 mg, 0.84 mmol) in water (2 ml), bis(triphenylphosphine) palladium(II) dichloride (24 mg, 0.021 mmol) were added. The reaction mixture was heated under microwave irradiation for 30 min at 120° C. The mixture was then diluted in ethyl acetate (50 ml), washed with 5% lithium chloride aqueous solution (3×20 ml), brine (20 ml) and the mixture concentrated in vacuo and purified by column (0-10% 7M ammonia in methanol/dichloromethane). Further purification by mass directed autoprep afforded the desired product as an off-white solid (11 mg, 0.02 mmol, 3% over 2 steps).

$^1$H NMR (300 MHz; CDCl$_3$) δ 2.09 (brs, 4H), 2.55 (t, 4H, J=4.3 Hz), 3.19 (brs, 6H), 3.75-3.69 (m, 6H), 3.88 (d, 2H, J=4.6 Hz), 7.54 (ddd, 1H, J=2.9 Hz, J=8.0 Hz, J=10.8 Hz), 7.93 (d, 2H, J=8.3 Hz), 8.20-8.11 (m, 2H), 8.32 (brs, 1H) ppm.

Purity by LCMS (UV Chromatogram, 190-450 nm) 95%, rt=1.52 min, m/z 499 (M+H)$^+$

EXAMPLE 9

2-(4-((1,1-dioxidothiomorpholino)methyl)phenyl)-6-fluoro-N-(2-(pyrrolidin-1-yl)ethyl)quinoline-4-carboxamide

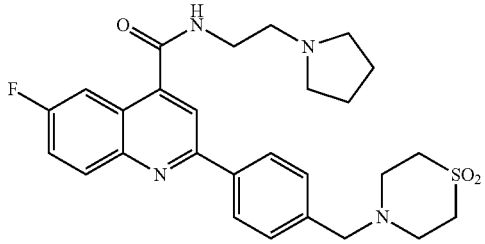 [SMILES: O=C(NCCN1CCCC1)c1cc(-c2ccc(CN3CCS(=O)(=O)CC3)cc2)nc2ccc(F)cc12]

To a solution of 4-(4-bromo-3-fluorobenzyl)thiomorpholine1,1-dioxide (283 mg, 0.93 mmol) in 1,4-dioxane (4 ml), bis(pinacolato)diboron (284 mg, 1.12 mmol), potassium acetate (201 mg, 2.05 mmol) and [1,1'-Bis(diphenylphosphino)ferrocene]dichloropalladium(II) (34 mg, 0.047 mmol) were added and the mixture was heated under microwave irradiation at 120° C. for 30 mins. The reaction mixture was concentrated under reduced pressure, diluted with dichloromethane (10 ml), washed with water (5 ml) and filtered through a phase separator. The filtrate was then concentrated under reduced pressure to afford boronic ester intermediate as determined by $^1$H NMR in CDCl$_3$.

Crude boronic ester was then dissolved in DMF (10 ml) and 2-chloro-6-fluoro-N-(2-(pyrrolidin-1-yl)ethyl)quinoline-4-carboxamide (150 mg, 0.81 mmol), potassium phosphate tribasic (198 mg, 0.93 mmol) in water (2 ml), bis(triphenylphosphine) palladium(II) dichloride (27 mg, 0.023 mmol) were added. The reaction mixture was heated under microwave irradiation for 30 mins at 120° C. The reaction crude was filtered through a Celite pad and washed with ethyl acetate (4×10 ml). The combined organic phases were washed with 5% lithium chloride aq. (3×10 ml), brine (10 ml), dried over magnesium sulphate and concentrated under reduced pressure. Mixture purified by mass directed autopreparative HPLC to afford the desired product as an off-white solid (64 mg, 0.13 mmol, 14% yield over 2 steps).

$^1$H NMR (500 MHz; CDCl3) δ 2.15-2.17 (m, 2H), 2.30-2.33 (m, 2H), 2.91 (brs, 2H), 3.04 (brs, 4H), 3.07 (brs, 4H), 3.42 (q, 2H, J=5.4 Hz), 3.73 (brs, 2H), 4.02-3.94 (m, 4H), 7.53-7.47 (m, 2H), 8.22-8.17 (m, 2H), 8.37 (d, 2H, J=8.0 Hz), 8.54 (s, 1H), 9.11 (brs, 1H), 12.57 (brs, 1H) ppm.

Purity by LCMS (UV Chromatogram, 190-450 nm) 95%, rt=5.50 min, m/z 511 (M+H)$^+$

EXAMPLE 10

2-(2-chloro-4-(morpholinomethyl)phenyl)-6-fluoro-N-(2-(pyrrolidin-1-yl)ethyl)quinoline-4-carboxamide

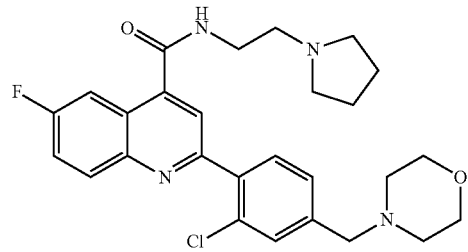 [SMILES: O=C(NCCN1CCCC1)c1cc(-c2ccc(CN3CCOCC3)cc2Cl)nc2ccc(F)cc12]

A mixture of 2-(2-chloro-4-(morpholinomethyl)phenyl)-6-fluoroquinoline-4-carboxylic acid (303 mg, 0.76 mmol) (preparation 18) in DCM (6 ml) was prepared at room temperature and N-methylmorpholine (0.166 ml, 1.51 mmol) and 2-chloro-4,6-dimethoxy-1,3,5-triazine (CDMT) (159 mg, 0.91 mmol) added and the mixture stirred for 1 h in a sealed vial. 2-(Pyrrolidin-1-yl)ethanamine (0.143 ml, 1.13 mmol) was then added and the mixture stirred in a sealed vial for 17 h. The mixture was then diluted with DCM (5 ml) and the organic layers washed with water (2×3 ml) and filtered through a phase separator and the organic layers concentrated under reduced pressure and purified by column chromatography (0-10% 7M NH3 in MeOH/DCM) to afford an off white solid. Analysis by 1HNMR showed impurities and the mixture was further purified by mass directed autopreparative HPLC to afford the desired product as an off-white solid (228 mg, 0.46 mmol, 61%).

$^1$H NMR (500 MHz; CDCl3) δ 1.76-1.79 (m, 4H), 2.49 (brs, 4H), 2.57 (brs, 4H), 2.75 (t, 2H, J=6.0 Hz), 3.55 (s, 2H), 3.65 (q, 2H, J=5.3 Hz), 3.74 (t, 4H, J=4.6 Hz), 6.82 (brs, 1H), 7.40 (dd, 1H, J=1.6, 7.9 Hz), 7.52-7.57 (m, 2H), 7.68 (d, 1H, J=7.9 Hz), 7.89 (s, 1H), 8.05 (dd, 1H, J=2.8, 10.0 Hz), 8.19 (dd, 1H, J=5.5, 9.2 Hz) ppm.

Purity by LCMS (UV Chromatogram, 190-450 nm) 95%, rt=5.2 min, m/z 497 (M+H)$^+$

EXAMPLE 11

2-(2-chloro-4-(morpholinomethyl)phenyl)-6-fluoro-N-(2-(pyrrolidin-1-yl)ethyl)quinoline-4-carboxamide; fumaric acid salt

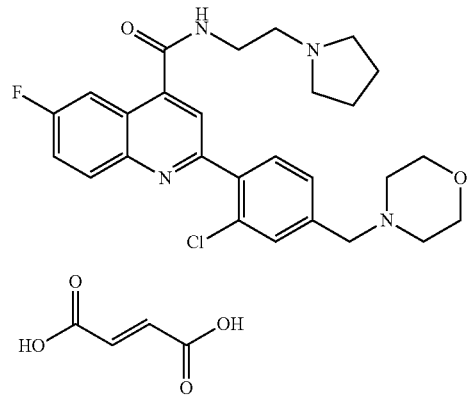 [SMILES: O=C(NCCN1CCCC1)c1cc(-c2ccc(CN3CCOCC3)cc2Cl)nc2ccc(F)cc12 ; O=C(O)/C=C/C(=O)O]

A mixture of 2-(2-chloro-4-(morpholinomethyl)phenyl)-6-fluoro-N-(2-(pyrrolidin-1-yl)ethyl)quinoline-4-carboxamide (example 10) (228 mg, 0.46 mmol) in MeOH (6 ml) was prepared at room temperature and a solution of fumaric acid (53 mg, 0.46 mmol) in EtOH (4 ml) was added dropwise over 1 minute and the mixture stirred at room temperature for 16 h. The mixture was then concentrated under reduced pressure and EtOH added (6 ml) and the mixture concentrated under reduced pressure. The mixture was then triturated in EtOAc, filtered, washed with EtOAc (3×10 ml) and dried under reduced pressure to afford the desired salt as an off-white solid (255 mg, 0.42 mmol, 91%).

$^1$H NMR (500 MHz; d6-DMSO) δ 1.75 (s, 4H), 2.41 (brs, 4H), 2.68 (brs, 4H), 2.77 (t, 2H, J=5.5 Hz), 3.51 (q, 2H, J=6.3 Hz), 3.57 (s, 2H), 3.60 (t, 4H, J=4.3 Hz), 6.54 (s, 2H), 7.46 (dd, 1H, J=1.4, 8.0 Hz), 7.57 (s, 1H), 7.67 (d, 1H, J=7.9 Hz), 7.79 (dt, 1H, J=3.0, 9.1 Hz), 7.85 (s, 1H), 8.11 (dd, 1H, J=2.9, 10.4 Hz), 8.18 (dd, 1H, J=5.5, 9.3 Hz), 8.89 (t, 1H, J=6.4 Hz), 12.99 (brs, 2H) ppm.

Purity by LCMS (UV Chromatogram, 190-450 nm) 95%, rt=5.2 min, m/z 497 (M+H)$^+$

The additional Examples in Table 6 may be prepared in accordance with the general methods detailed hereinbefore for Example 1, via firstly preparation of the requisite boronic acids from the appropriate starting materials, in accordance with the methodology of Preparation 2, followed by reaction with Preparation 4 in accordance with the methodology described in the preparation of Example 1 in order to furnish Example compounds 12 or 13.

The invention claimed is:

1. A compound of formula I

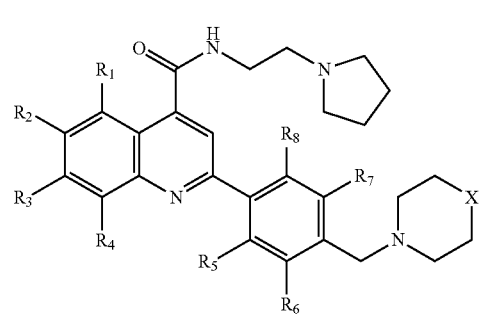

wherein $R^1$, $R^2$, $R^3$, $R^4$, $R^5$, $R^6$, $R^7$ and $R^8$ are independently of each other selected from: H, Cl or F; wherein the pyrrolidinyl, morpholinyl or thiomorpholinyl dioxide heterocyclic groups are independently optionally substituted by one or more Cl, F or —($C_1$-$C_3$) alkyl groups; and wherein X is —O— or —$SO_2$—;

or a pharmaceutically acceptable salt, hydrate, solvate, or polymorph thereof.

2. The compound of claim 1 wherein X is —O—.

3. The compound of claim 1 wherein $R^1$ and $R^2$ are independently selected from H or F.

4. The compound of claim 1 wherein X is —O— and wherein $R^1$ and $R^2$ are independently selected from H or F.

TABLE 6

| Example number | Structure | Starting materials |
|---|---|---|
| 12 | 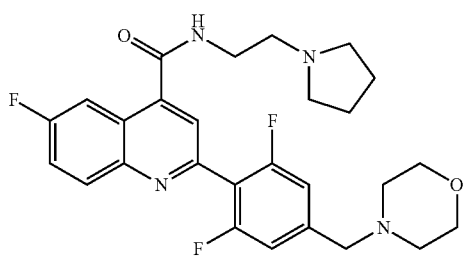 [SMILES: O=C(NCCN1CCCC1)c1cc(-c2c(F)cc(CN3CCOCC3)cc2F)nc2ccc(F)cc12] | Preparation 4 |
| 13 | 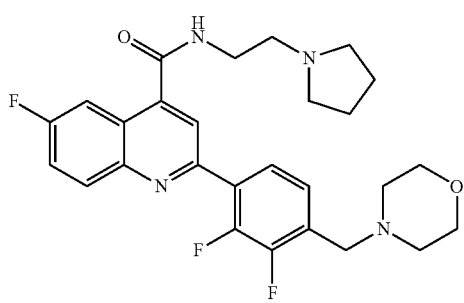 [SMILES: O=C(NCCN1CCCC1)c1cc(-c2ccc(CN3CCOCC3)c(F)c2F)nc2ccc(F)cc12] | Preparation 4 |

5. The compound of claim 1 wherein $R^1$ and $R^2$ are independently selected from H or Cl.

6. The compound of claim 1 wherein X is —O— and wherein $R^1$ and $R^2$ are independently selected from H or Cl.

7. The compound of claim 1 wherein $R^3$ and $R^4$ are each independently selected from H or F.

8. The compound of claim 1 wherein X is —O— and wherein $R^3$ and $R^4$ are each independently selected from H or F.

9. The compound of claim 1 wherein one or two of $R^1$, $R^2$, $R^3$, and $R^4$ are F and/or Cl.

10. The compound of claim 1 wherein X is —O— and wherein one or two of $R^1$, $R^2$, $R^3$, and $R^4$ are F and/or Cl.

11. The compound of claim 1 wherein the phenyl ring is mono-, di- or tri- substituted with F and/or Cl.

12. The compound of claim 1 wherein X is —O— and wherein the phenyl ring is mono-, di- or tri- substituted with F and/or Cl.

13. The compound of claim 1 wherein the phenyl ring is mono-substituted and wherein $R^5$ and/or $R^8$ are each independently selected from H or F.

14. The compound of claim 1 wherein $R^3$, $R^4$, $R^5$, $R^6$ and $R^7$ are independently selected from H or F.

15. A compound according to claim 1 independently selected from:
- 6- Fluoro-2-[4-(morpholinomethyl)phenyl]-N-(2-pyrrolidin-1-ylethyl)quinoline-4-carboxamide;
- 6- Fluoro-2-[4-(morpholinomethyl)phenyl]-N-(2-pyrrolidin-1-ylethyl)quinoline-4-carboxamide fumaric acid salt;
- 6-chloro-2-[4-(morpholinomethyl)phenyl]-N-(2-pyrrolidin-1-ylethyl)quinoline-4-carboxamide;
- 2-[4-(morpholinomethyl)phenyl]-N-(2-pyrrolidin-1-ylethyl)quinoline-4-carboxamide;
- 6-fluoro-2-(3-fluoro-4-(morpholinomethyl)phenyl)-N-(2-(pyrrolidin-1-yl)ethyl)quinoline-4-carboxamide;
- 2-[4-(morpholinomethyl)phenyl]-N-(2-pyrrolidin-1-ylethyl)quinoline-4-carboxamide fumaric acid salt;
- 6-fluoro-2-(2-fluoro-4-(morpholinomethyl)phenyl)-N-(2-(pyrrolidin-1-yl)ethyl)quinoline-4-carboxamide;
- 2-(3,5-difluoro-4-(morpholinomethyl)phenyl)-6-fluoro-N-(2-(pyrrolidin-1-yl)ethyl)quinoline-4-carboxamide;
- 2-(4-((1,1-dioxidothiomorpholino)methyl)phenyl)-6-fluoro-N-(2-(pyrrolidin-1-yl)ethyl)quinoline-4-carboxamide;
- 2-(2,6-difluoro-4-(morpholinomethyl)phenyl-6-fluoro-N-(2-(pyrrolidin-1-yl)ethyl)quinoline-4-carboxamide;
- 2-(2,3-difluoro-4-(morpholinomethyl)phenyl-6-fluoro-N-(2-(pyrrolidin-1-yl)ethyl)quinoline-4-carboxamide;
- 2-(2-chloro-4-(morpholinomethyl)phenyl)-6-fluoro-N-(2-(pyrrolidin-1-yl)ethyl)quinoline-4-carboxamide;
- 2-(2-chloro-4-(morpholinomethyl)phenyl)-6-fluoro-N-(2-(pyrrolidin-1-yl)ethyl)quinoline-4-carboxamide fumaric acid salt;

or a pharmaceutically acceptable salt, hydrate, solvate, or polymorph thereof.

16. A compound of claim 1 having Pf3D7 functional potency of less than about 0.1 micromolar (µM).

17. A compound of claim 1 having Pf3D7 functional potency of less than about 0.05 micromolar (µM).

18. A compound of formula (I) or a pharmaceutically acceptable, salt, solvate, hydrate, or polymorph thereof in accordance with claim 1 for use as a medicament.

19. A compound of formula (I) or a pharmaceutically acceptable, salt, solvate, hydrate, or polymorph thereof in accordance with claim 1 for use in the treatment of malaria.

20. A pharmaceutical composition comprising a compound of formula (I) or a pharmaceutically acceptable, salt, solvate, hydrate, or polymorph thereof in accordance with claim 1, together with one or more pharmaceutically acceptable carriers, diluents or excipients.

21. The pharmaceutical composition of claim 20 wherein the compound has Pf3D7 functional potency of less than about 0.05 micromolar (µM).

* * * * *